United States Patent
Laquidara et al.

(10) Patent No.: US 9,575,046 B1
(45) Date of Patent: Feb. 21, 2017

(54) EXPLOSIVE DETECTION COMPOSITIONS AND KIT

(71) Applicants: Joseph M. Laquidara, Westwood, NJ (US); Christopher D. Applegate, Andover, NJ (US)

(72) Inventors: Joseph M. Laquidara, Westwood, NJ (US); Christopher D. Applegate, Andover, NJ (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 28 days.

(21) Appl. No.: 14/933,657

(22) Filed: Nov. 5, 2015

(51) Int. Cl.
| | |
|---|---|
| *G01N 33/22* | (2006.01) |
| *G01N 33/00* | (2006.01) |
| *G01N 33/28* | (2006.01) |
| *G01N 31/22* | (2006.01) |
| *G01N 21/64* | (2006.01) |
| *G01N 33/58* | (2006.01) |

(52) U.S. Cl.
CPC ......... *G01N 33/227* (2013.01); *G01N 21/6428* (2013.01); *G01N 31/22* (2013.01); *G01N 33/0039* (2013.01); *G01N 33/2882* (2013.01); *G01N 33/582* (2013.01)

(58) Field of Classification Search
CPC .. G01N 31/22; G01N 21/6428; G01N 33/582; G01N 33/2882; G01N 33/0039; C10L 1/003; C12Q 33/0039
See application file for complete search history.

(56) References Cited

U.S. PATENT DOCUMENTS

| | | |
|---|---|---|
| 3,718,433 A | 2/1973 | Emmet |
| 5,296,380 A | 3/1994 | Margalit |
| 7,846,740 B2 | 12/2010 | Amisar |
| 8,056,498 B2 | 11/2011 | Holt |
| 2011/0129394 A1 | 6/2011 | Holt |

OTHER PUBLICATIONS

Standard Range Lab Nitrate Test Kit, The Nitrate Elimination Co, 2012, Lake Linden Michigan.
Searle, Philip L., The Berthelot or Indophenol Reaction and Its Use in the Analytical Chemistry of Nitrogen, May 1984, 109, 549-568, New Zealand Soil Bureau, New Zealand.
Griess Reagent Kit for Nitrite Detection, Molecular Probes, Jul. 9, 2003, U.S.
Emmet, Robert T., Spectrophotmetric Determination of Urea and Natural Waters with Hypochlorite and Phenol, May 1969, Naval Ship Research and Development Center, Annapolis MD.

*Primary Examiner* — Krishnan S Menon
*Assistant Examiner* — Dwan A Gerido
(74) *Attorney, Agent, or Firm* — Lisa H. Wang

(57) ABSTRACT

Explosive reagent detecting compositions are provided for detecting explosives containing chlorate and hydrogen peroxide. Such compositions include Ru-EDTA complexes, binuclear aromatic hydroxyl (BAH) and an optional lanthanide salt. Embodiments of these compositions may be combined with a compact and flexible packaging as an easy-to-use kit for detecting the presence of explosives.

15 Claims, 30 Drawing Sheets

EXPLOSIVE DETECTION COMPOSITIONS AND KIT

RIGHTS OF THE GOVERNMENT

The inventions described herein may be manufactured and used by or for the United States Government for government purposes without payment of any royalties.

FIELD OF INVENTION

The present invention is related to colorimetric explosive detection kits comprising an easy-to-use packaging and novel explosive detection reagents. In one exemplary embodiment, the novel explosive detection reagent comprises rutheniumethylenediaminetetraacetate (Ru-EDTA) complex and a binuclear aromatic hydroxyl (BAH) compound for detection of chlorates and hydrogen peroxide.

BACKGROUND OF THE INVENTION

Home Made Explosives (HME) and Improved Explosive Devices (IED) are weapons of choice for terrorists worldwide and at home. Critical to the safety of our service members and the public are uncovering these HMEs and IEDs before they are employed as well as investigating an incident after it occurs to prevent future occurrences. The ability to detect trace or residue explosive material can make a significant impact in prevention, mitigation and deterrence in the global effort against terrorists.

Traditional explosive detection devices uses instruments such as portable electronic devices, raman spectroscopy, capillary electrophoresis, laser electrospray with mass spectrometry, ion chromatography, and laser induced breakdown spectroscopy. Use of such instruments require specialize equipment and training, a large budget and regular maintenance. While these devices are useful, their costs, training, and limited portability may not be ideal for use by soldiers on the field. Alternatives to instruments for detecting explosives uses colorimetric explosive detection kits which detect the presence of explosives or a key ingredient in the explosive by a visual color change. This is attributed to a unique chemical reaction between the chemical of interest and a reagent. Colorimetric methods rely on several chemical reagents used in a sequence of steps to perform the necessary reaction for a color change to occur. Typically these detection capabilities rely on highly specific reactions to confidently determine the explosive present.

Much effort has been developed in the detection of a number of explosives including those that contain chlorate, hydrogen peroxide, ammonium, urea and nitrates. For instance, postassium salt of chlorate is a strong oxidizer, readily available and easily detonable when mixed with fuel. Numerous examples of HMEs exist that contain postassium chlorate such as Armstrong's mixture, black powder variants, poor man's C-4, and Sprengel explosive. Hydrogen peroxide is a strong liquid oxidizer and a critical ingredient in the preparation of explosive organic peroxides such as triacetone peroxide (TATP), hexamethylenetriperoxidediamine (HMTD), and methly ethyl ketone peroxide (MEKP). The detection of hydrogen peroxide is a good indicator for the presence of these explosive peroxides. Ammonium and urea nitrates found in fertilizers are also common in HMEs because of its widespread accessibility and ease for concealment as an agricultural use product.

Colorimetric detection of explosives are generally known in the literature. For example, U.S. Pat. No. 7,846,740 titled "Method and Kit for detecting explosive substances containing certain oxidants" describes the blue color formation of chlorate detection when treated with the chemical reagent diphenylamine in the presence of sulfuric acid, dimethyl sulfoxide and ethanol. In this case the oxidation of diphenyl amine produces a colored compound which is presumably the meriquinoidal diphenylbenzidine blue intermediate known from the literature. Other colored reactions occur which have a similar reaction mechanism and collectively these are known as redox reactions. Typically redox reaction with chlorate occur with a number of aromatic amines and aromatic alcohol derivatives.

Still other methods of non-instrumented color detection chemistries of chlorate detection exist. For example, manganous sulphate in concentrated phosphoric acid reacts with chlorate to produce the violet manganic-phosphate ion. A different method for the detection of chlorate uses ammonium thiocyanate catalyzed by iron to produce a yellow color change from the oxidation of thiocyanate; however, both of these methods require heat to facilitate the reaction to occur in a timely manner.

Hydrogen peroxide is also detected by redox chemistry. Probably the most common method for the detection is the iodine-starch test. Other methods include the oxidation of ferrous ions and reaction with xylenol orange, peroxidase enzyme reactions, and a number of metal oxidations that include iron, copper, and vanadium complexes to list a few. The detection of hydrogen peroxide is a suitable indicator for the presence of organic peroxide containing HMEs. Typically this requires a stepwise procedure that begins with the decomposition of the organic peroxide to produce hydrogen peroxide followed by a second reaction step for identification.

Commercially available colorimetric kits for the detection of explosive compounds are available but with varying levels of success. A few such kits are Explosive Testing Kit (ETK) from Lindon Defense, Elite Test Kit from Field Forensics, Inc., and DropEx kits from Mistral Security, Inc. These kits use liquid reagents (sometimes in multi-step sequences) to react with the suspected explosive to perform the necessary chemical reaction for a color change to occur. This approach is sometimes referred as wet chemical analysis.

Current liquid explosive detection kits require the user to premix liquid chemicals using multiple vials of liquids and performing serial analysis using specialized collection equipment typically packaged in a bulky container. The drawbacks associated with liquid explosive detection kits is the inherent risk of liquid reagent spillage. In cases where hazardous chemicals are used (such as strong acids) personal safety equipment such as gloves and glasses are highly recommended. In addition, spillage and unintentional mixing of liquid reagents may lead to unreliable results. All of these limitations to liquid explosive detection kits can be difficult for use on the field or under stressful situations. Thus, a need exist for an easy-to-use portable, safe, fast and reliable colorimetric explosive detection kit.

SUMMARY OF THE INVENTION

The primary object of the present invention is to provide an explosive detection kit that is portable, easy-to-use, fast, reliable and safe to use on humans. Disclosed herein are kits comprising detection reagent compositions and flexible packaging that protects the reactants and serves as a vessel for the chemical reaction and analysis. The kit's compactness and packaging allows it to be stored in pockets or other small spaces in a ready-to-use system for immediate detection and analysis. The kit can be used by military, law enforcement and intelligence personnel for safe, quick and reliable determination of suspected explosive chemicals.

According to one aspect of the present invention, the flexible explosive detection package comprises a flexible substrate, a collection assembly, a detection reagent composition and a cover disposed on the substrate, wherein the detection reagent composition has a defined geometric shape and is position lateral to the collection assembly to permit contact of detection reagent composition with the collection assembly when folded.

In another aspect of the present invention, the explosive detection reagent composition comprises rutheniumethylenediaminetetraacetate (RuEDTA) complex and binuclear nuclear aromatic hydroxyl (BAH) compound and a lanthanum salt for detecting explosives containing chlorate and hydrogen peroxide.

In another aspect of the present invention, the explosive detection reagent composition comprises sodium phenoxide as a first detection reagent and an oxidizer and a catalyst as a second detection reagent composition for detecting explosives containing ammonia and urea.

In yet another aspect of the present invention, the explosive detection reagent composition comprises sodium phenoxide as a first detection reagent and SDCC, sodium nitroprusside, and sodium carbonate as a second detection reagent composition for detecting explosives containing ammonia and urea.

In accordance with a further aspect of the invention, the explosive detection reagent composition comprises either tartaric or citric acid, sulfanilamide, N-(1-Naphthyl)ethylenediamine dihydrochloride, and zinc powder as a detection reagent composition for detecting explosives containing nitrates.

The explosive detection kit described herein may be utilized to detect suspected explosives according to the following steps: (1) exposing the collection pad 230; (2) contacting the suspected explosive residue with the collection pad 230; (3) exposing the detection reagent 20; (4) contacting the detection reagent composition 20 with the collection pad 230 containing the sample; (5) and observing the color change for comparison against a reference standard to determine the presence and type of explosive. The process of step (4) may be repeated with more than one detection reagent composition 20.

DETAILED DESCRIPTION

Figure 3:
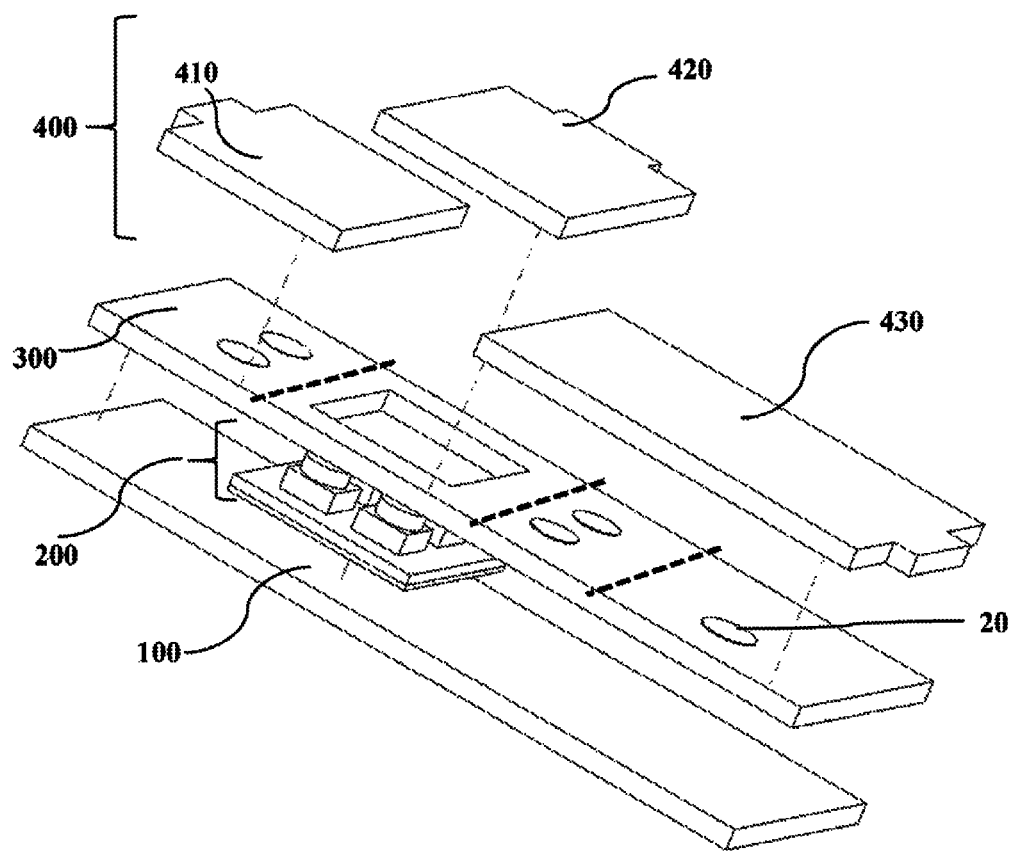
FIG. 3 is an exploded view of assembled explosive detection package of a first embodiment.
Figures 4A, 4B:
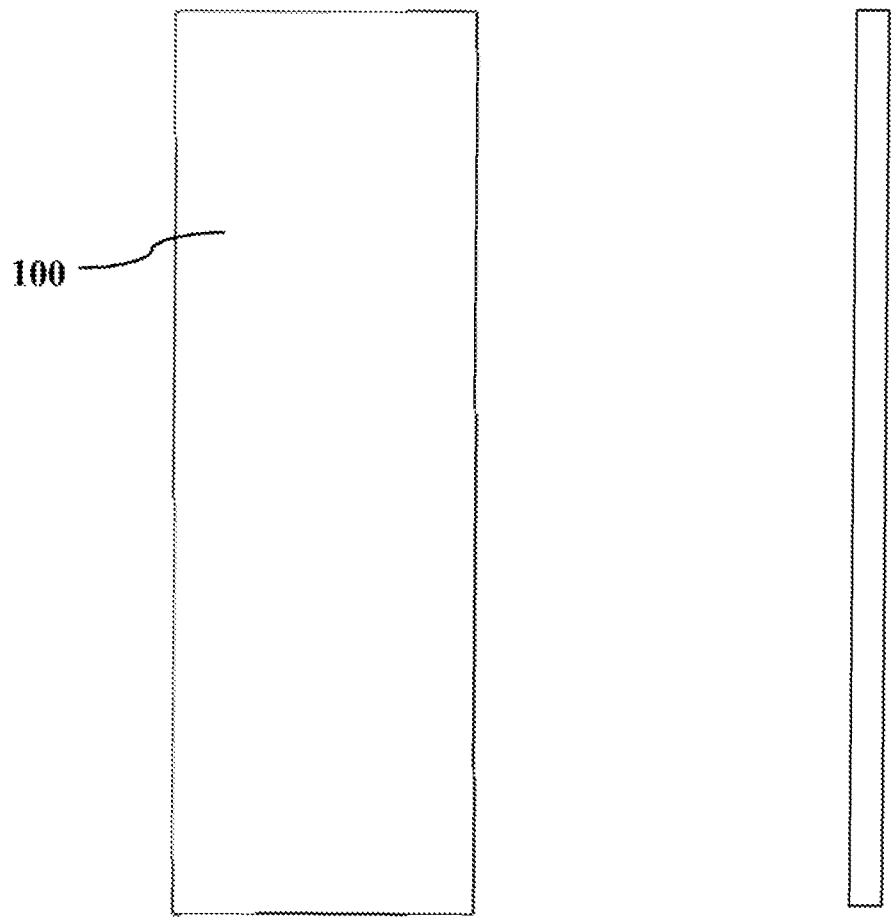
FIG. 4A is the front view of the substrate element of FIG. 3.
FIG. 4B is the side view of the substrate element of FIG. 4A.
Figure 5A:
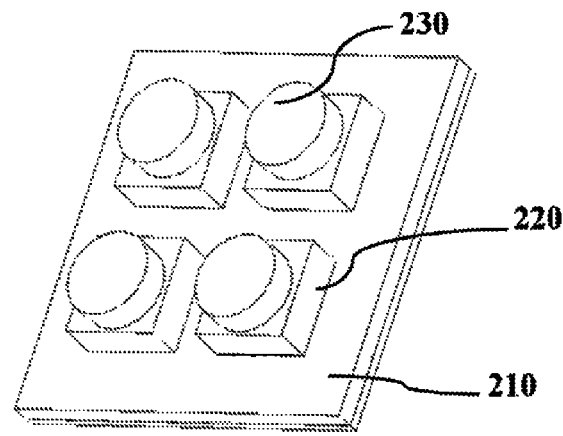
FIG. 5A is a perspective view of the collection assembly FIG. 3.
Figure 5B:
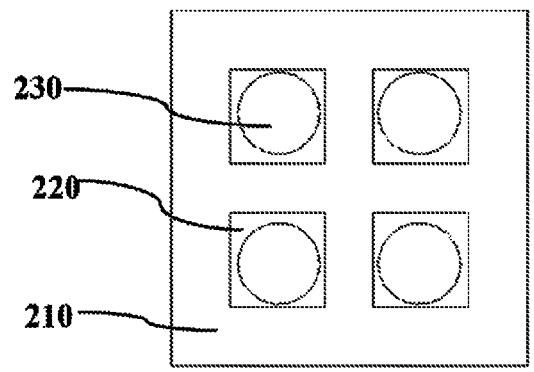
FIG. 5B is a top view of the collection assembly of FIG. 3.
Figure 5C:
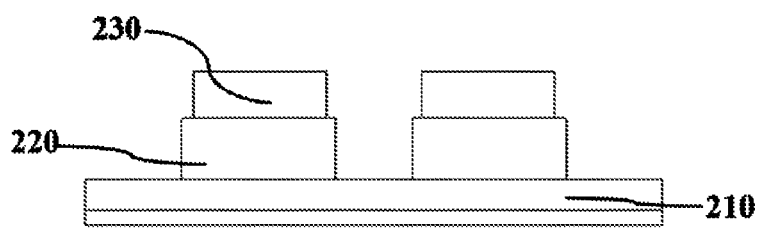
FIG. 5C is an elevational view of the collection assembly of FIG. 3.
Figures 6A, 6B:
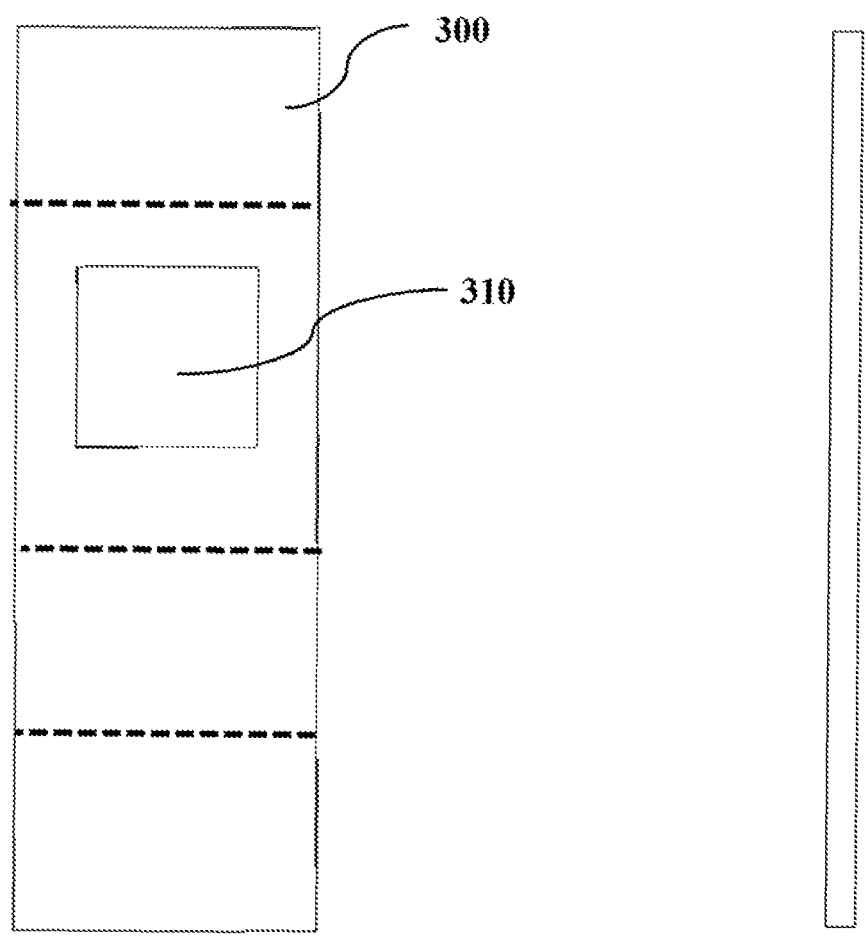
FIG. 6A is a front view of the liner assembly of FIG. 3.
FIG. 6B is a side view of the liner assembly of FIG. 6A.
Figures 7A, 7B:
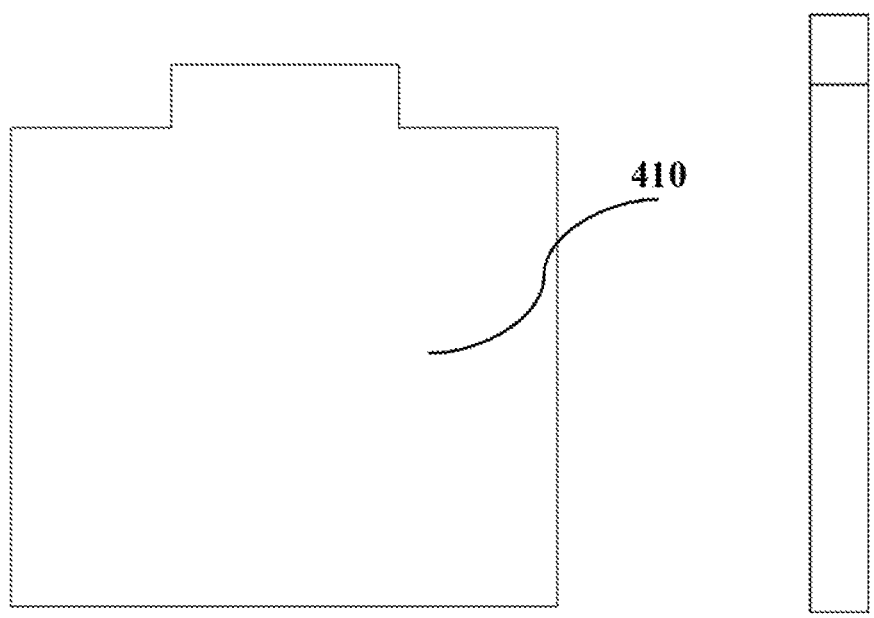
FIG. 7A is a front view of the cover for a first reagent detection area of FIG. 3.
FIG. 7B is a side view of the cover for a first reagent detection area of FIG. 7A.
Figures 8A, 8B:
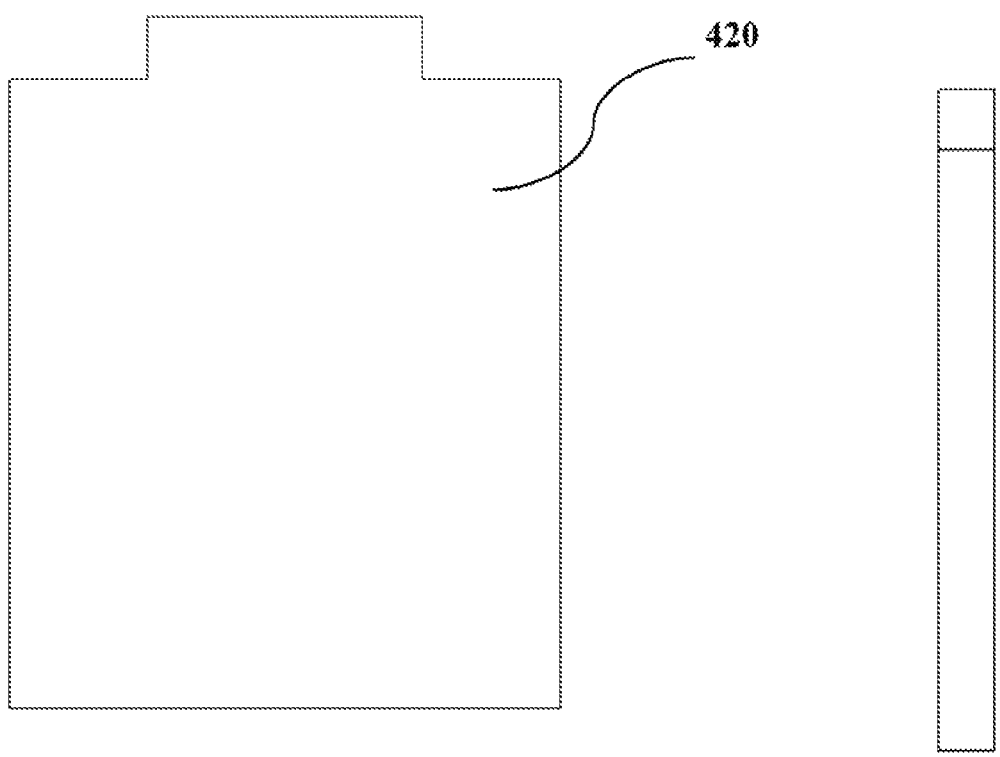
FIG. 8A is front view of a cover for the collection assembly of FIG. 3.
FIG. 8B is side view of a cover for the collection assembly of FIG. 8A.
Figures 9A, 9B:
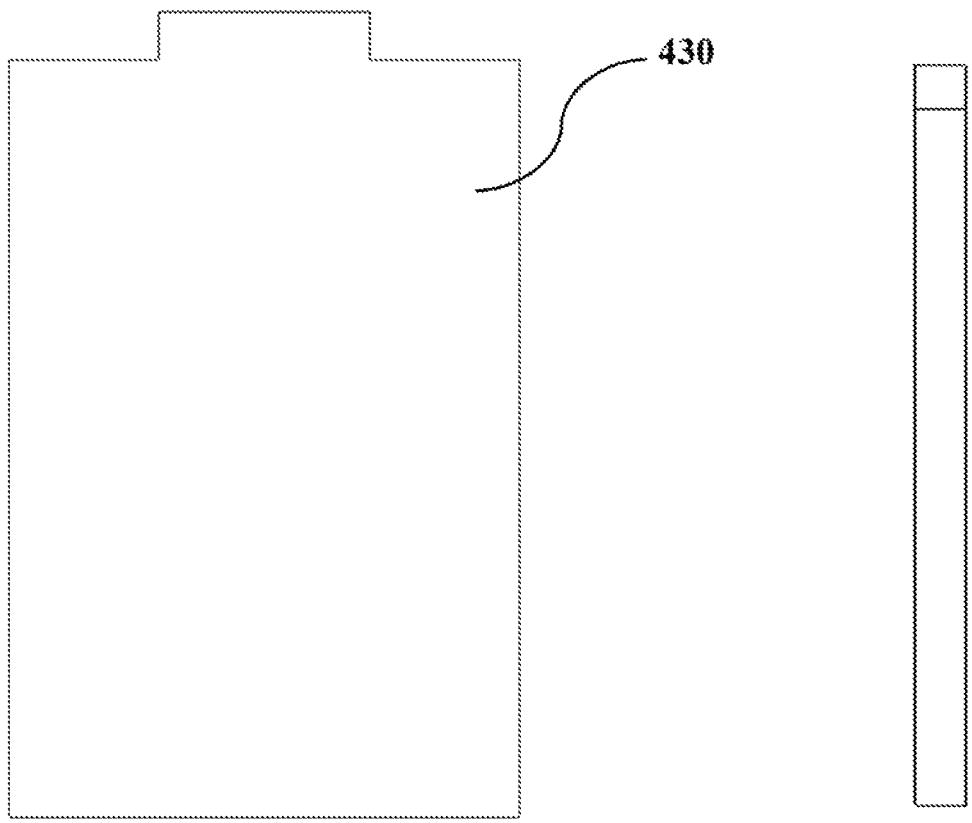
FIG. 9A is front view of a cover for a second and third reagent detection area of FIG. 3.
FIG. 9B is side view of a cover for a second and third reagent detection area of FIG. 3.
Figure 10:
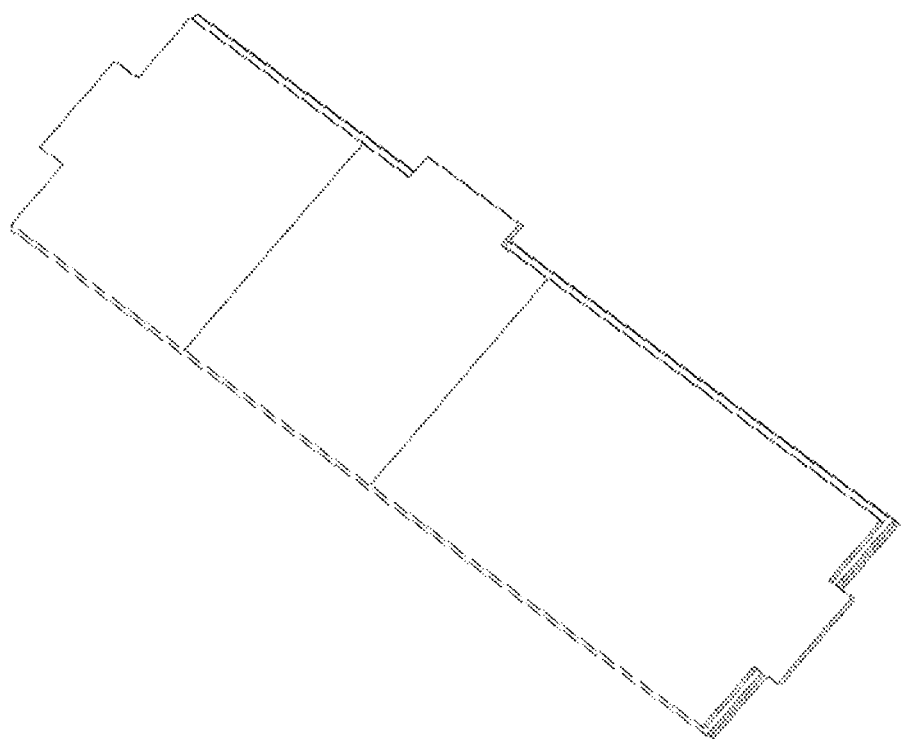
FIG. 10 is a top perspective view of a fully assembled explosive detection kit of FIG. 3.
Figure 11:
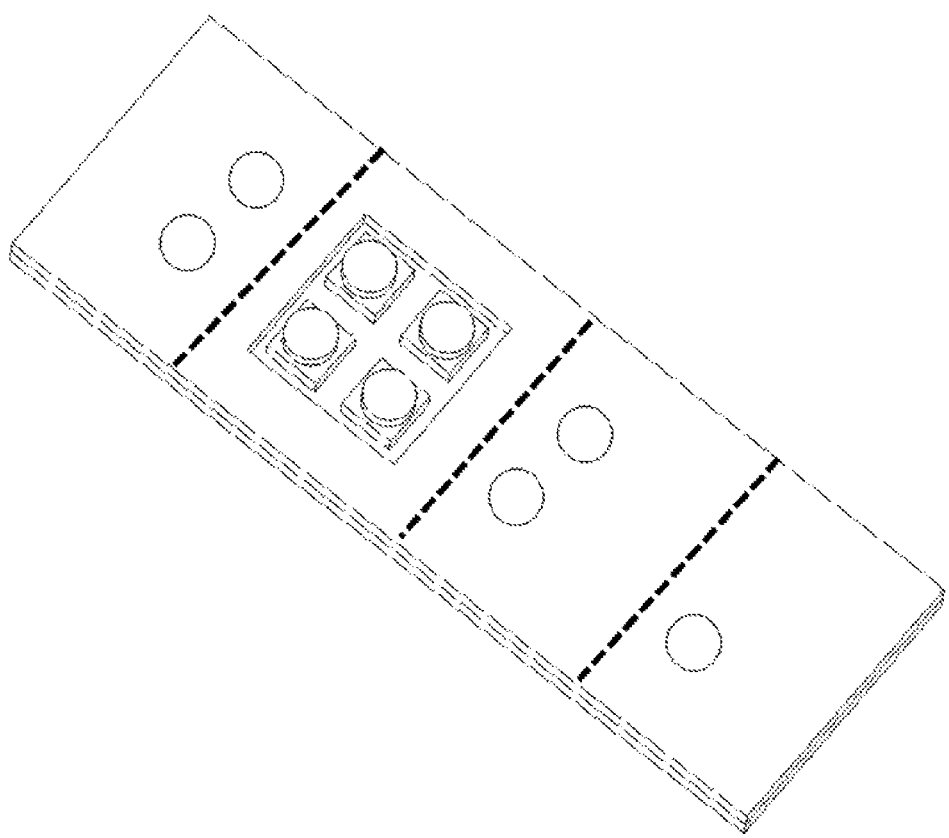
FIG. 11 is a top perspective view of assembled explosive detection kit of FIG. 3 with the covers removed.
Figure 12:
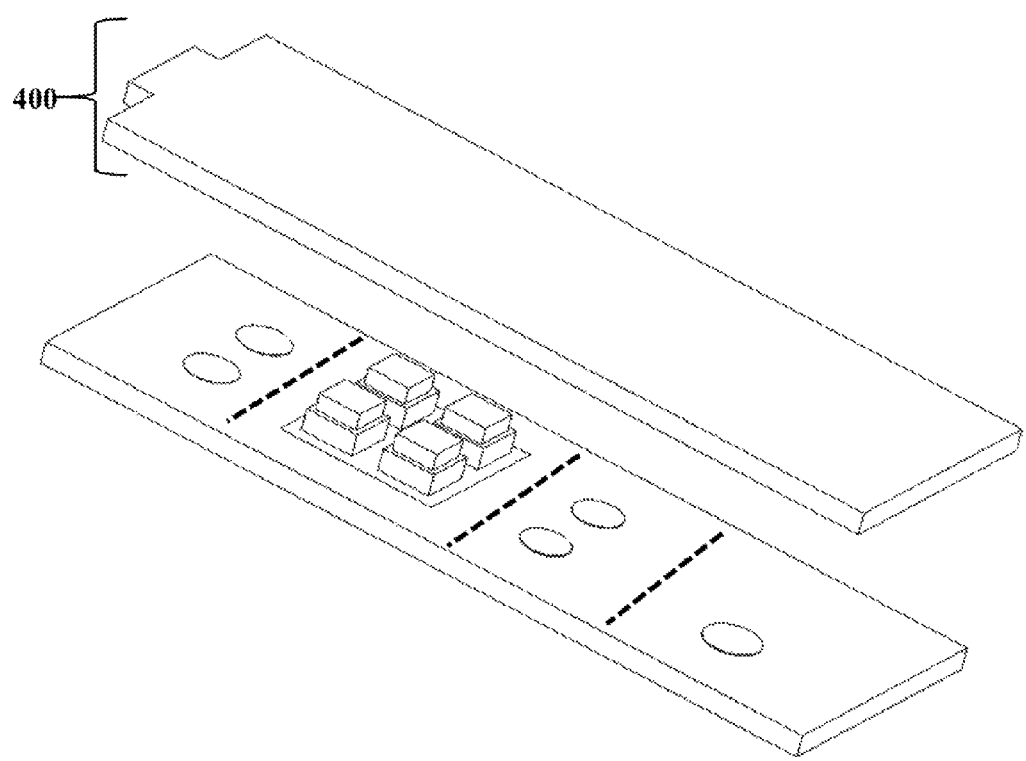
FIG. 12 is perspective view of a second embodiment of an explosive detection kit embodiment.
Figure 13:
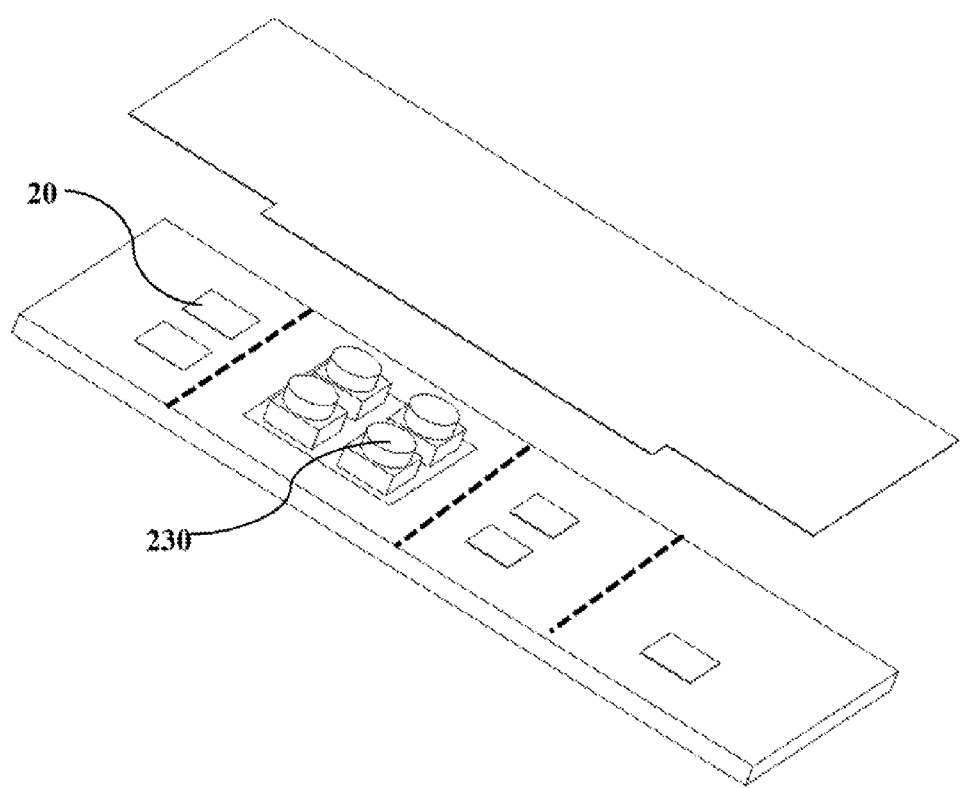
FIG. 13 is perspective view of a third embodiment of an explosive detection kit embodiment.
Figure 14:
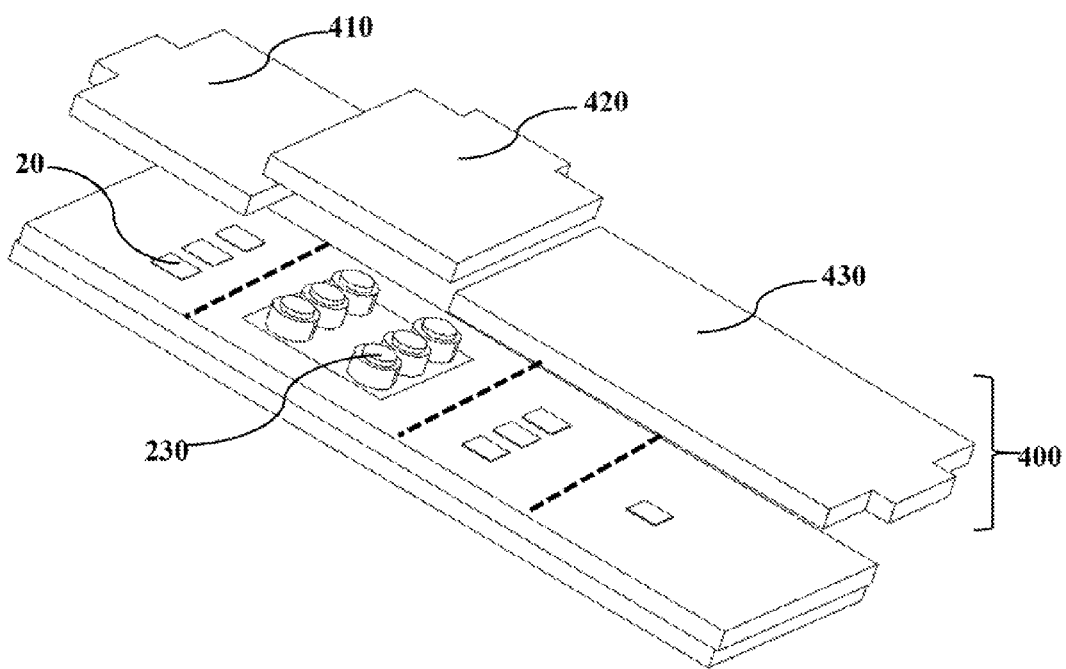
FIG. 14 is perspective view of a fourth embodiment of an explosive detection kit embodiment.
Figure 15:
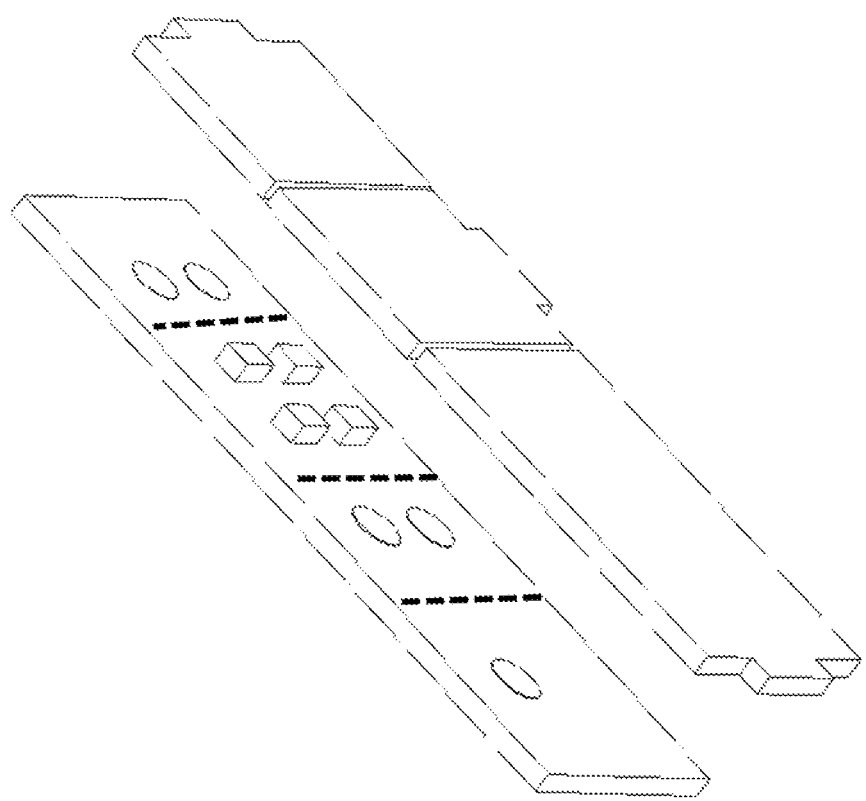
FIG. 15 is perspective view of a fifth embodiment of an explosive detection kit embodiment.
Figure 16:
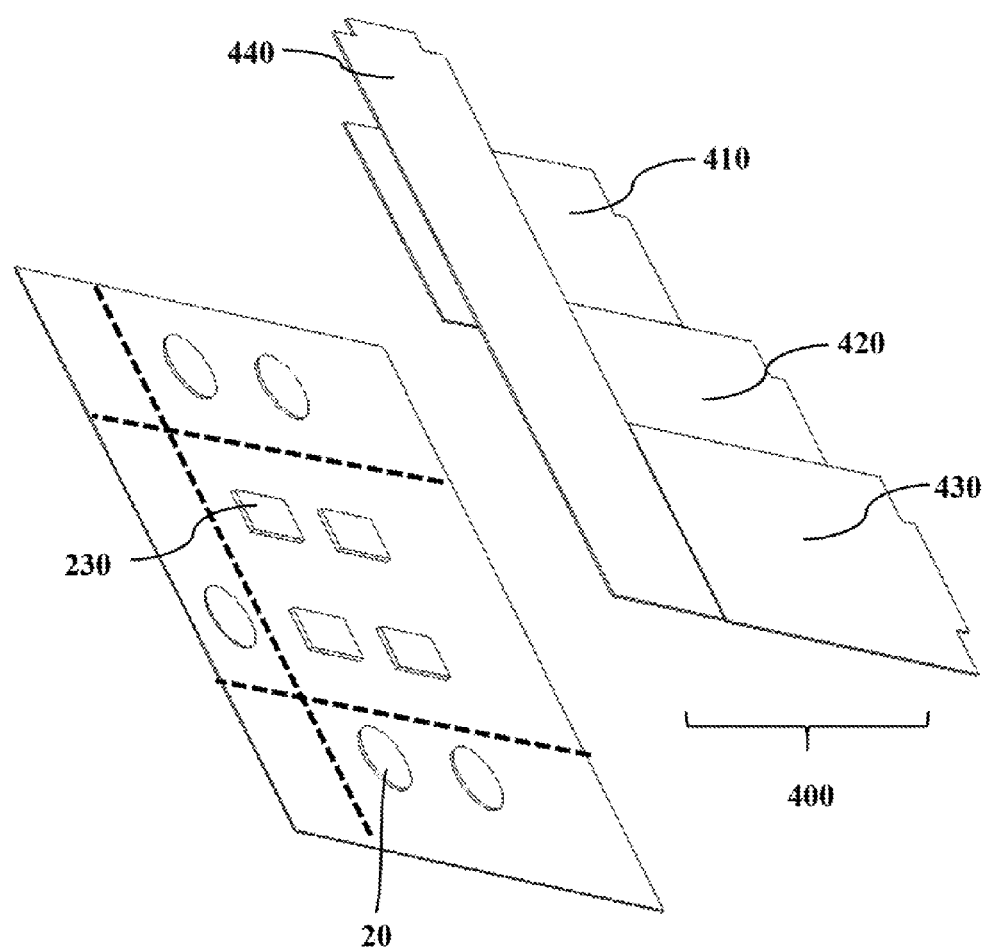
FIG. 16 is perspective view of a sixth embodiment of an explosive detection kit embodiment.

The present invention is directed to explosive detection kits comprising explosive detection reagents and storage of such detection reagents in a simple easy-to-use packaging that facilitates collection and detection of suspected explosive residue. The explosive detection kit 10 is composed of the packaging and the reagent detection composition 20. The arrangement and construction of a number of embodiments of the explosive detection kit 10 is shown in FIGS. 3-16. The dotted lines indicated in FIGS. 3-16 represent optional folds to facilitate contact of the detection reagents with the collection pad surface and to allow for storage of the explosive detection kit inside pockets or small spaces. FIG. 3 represents one embodiment of the explosive detection kit 10 described herein. FIGS. 4-16 represents additional embodiments of the kits contemplated herein.

Explosive Detection Packaging

Referring to FIG. 3, the packaging comprises a substrate 100, collection assembly 200, an optional liner 300, and the cover assembly 400 which are described in more detail below. The explosive detection packaging containing the detection reagent 20 may be referred to collectively as a kit.

The substrate 100 may be composed of any barrier liner material that is thin, flexible, lightweight, and provides water-proof as well as water-vapor-proof protection. The material should also has the ability to be heat-sealed. Examples of materials useful as a substrate include MIL-PRF-131, MIL-PRF-22191, T90, Protect Calvac 6X, Protect Calvac 6X-5.0.

The collection assembly 200 is composed of the sample collection pad 230 having a surface, a platform 220 for supporting the collection pad, and a collection liner 210. The sample collection assembly 200 functions to collect the suspected explosive residue and provides a means for the chemical reaction between the residue and the detection reagent to occur.

The sample collection pad 230 comprises any absorbant material that is inert to chemical reactions. Preferably, the collection pad may be composed of any material having one or more of the following characteristics: absorbant, retains color, low in lint, comprises large fiber strands and tow in nitrogen content to avoid false positive results. Preferred materials comprising the collection pad include cotton fibers, wood pulp, synthetic fibers or a blend.

The collection pad is impregnated with a liquid solvent that is compatible with the detection reagent. Such liquid solvents will facilitate the chemical reaction between the detection reagents and the suspected explosive and is safe for human contact. Examples of liquid solvents include water or water based solutions. Additives such as preservatives, salts, and surfactants may be added to improve the solubility of explosive residue, maintain its efficacy under extreme environmental conditions (i.e. resist freezing at low temperatures), or promote stability of the reacting components. Any preservatives or additives that are added to the solvent should also be inert to the tested materials and safe for human contact. It is contemplated that the collection pad containing the solvent is in a ready-to-use state such that once the collection assembly cover 420 is removed, no additional components or steps are needed to collect the sample.

The collection assembly 200 may comprise a single collection member (consisting of at least one collection pad and its corresponding platform) or a plurality of collection members that are configured into any geometric shape. For ease of illustration, the geometric configuration of the collection member is in a 2×2, square pattern, where each collection pad may be approximately 0.35 inches long, 0.35 inches wide, and 0.1 inches in height with a tolerance of +0.0625 inches. The dimension and configuration may be modified depending on the type of testing to be performed and the corresponding reagents for the test. Alternative configurations contemplated may include 3×3, 4×4, 2×3, 3×2, 1×1, etc. Any geometric shape (i.e. circle, rectangles, triangle, octagon, lines, wavy lines, patches, etc. . . . ) may be adopted for the collection pad so long as it facilitates sample collection and detection.

The collection pads are placed on a single or plurality of platforms 220 made from inert high-density polyethylene (HDPE) or any other material that is safe for human contact and that blocks the transmission of the solvent solution. The dimensions for the platform may be slightly larger than the pad to accommodate the pad containing the liquid solvent. Suggested dimensions are approximately 0.4 inches long, 0.4 inches wide, and 0.13 inches in height with a tolerance of ±0.0625 inches. The suggested dimensions and tolerances can be modified to avoid distortion or cross-contamination of the reagents and sample. As illustrated in the embodiment of FIG. 3, the platforms are cube shape, however, any geometric shape (i.e. cylinder) and configuration of platforms can be utilized. The shape of the platforms may be independent of the collection pad.

An optional support surface such as a collection liner 210 may be attached to the bottom of the collection pact 230 and platform 220 to prevent cross-contamination of the solvent or the detection reagents by collecting any excess liquid (i.e. catch basin) that overflows from the collection pad. Any absorbant material may be utilized for the support surface including the same material used for the collection pads. An example of a proposed dimension for the collection liner 210 may be 2.1 inches long, 1.9 inches wide, and 0.05 inches in height with a tolerance of ±0.0625 inches, however, the sample dimension and tolerance may be modified to fit the dimensions of the packaging and its functions as a catch basin. Alternatives means may be utilized to substitute for the collection liner 210 such that it is functionally equivalent. Contemplated means for diverting or catching overflow liquids include channels, grooves or ridges.

The collection assembly 200 may optionally be disposed through the cavity of a liner 300 or rest directly on the liner 300. The liner 300 provides a support surface for the detection reagents and covers. The liner 300 may be heat sealed, applied with adhesive, or any other equivalent method that would affix the liner to the rest of the product. In one embodiment illustrated in FIG. 3, the liner is affixed directly to the substrate 100. Materials utilized for constructing the liner should be water-vapor-proof, moisture proof, and safe for human contact. Source materials useful for constructing the liner include MIL-PRF-131, MIL-PRF-22191, T90, Protect Calvac 6X, Protect Calvac 6X-5.0. The liner or the substrate surfaces may further comprise reference markings, instructions, directions or instructions for use of the explosive detection kit.

The collection assembly 200 and the detection reagent composition 20 may be covered by a single cover or a plurality of covers, cover assembly 400. The cover assembly 400 functions to protect the collection assembly 200 and the detection reagent 20 composition from environmental exposure and contaminants until the product is ready for use. These covers may be heat sealed, applied with adhesive, or any other equivalent method that will seal the cover to the rest of the product. Any means of sealing must also allow the cover to be easily pulled or removed from the detection reagents without disturbing the integrity of the reagents. Additionally it must also be water-vapor-proof, moisture proof, and safe for human contact. It is preferred that the detection reagents are sealed in separate compartments so that they do not cross-contaminate each other. This sealing in separate compartments does not affect the ability of the cover to be pulled off or removed and methods for affixing the separate covers may be used as previously described. The collection assembly cover 420 may be placed over the collection assembly 200 to shield and protect the collection assembly. The cover 420 also functions to prevention evaporation of the liquid solvent in the collection pad.

Additional covers (i.e. reagent composition cover 410 and reagent composition cover 430) may be located on either side of the collection assembly as illustrated in FIG. 3. These covers have the same properties and characteristics as the cover for the collection assembly 420.

The chemical composition of the detection reagent 20 disposed on the explosive detection package is further described below. The placement of the detection reagents on the packaging can vary so long as when the packaging is folded over, the detection reagents (either in solid or liquid form) comes in contact with the collected sample to facilitate a chemical reaction and do not cross-contaminate other samples or detection reagents. Placement of the detection reagents lateral to the collection pad or collection assembly is preferred as it permits maximum contact between the reagents and the collection pad when the packaging is folded over.

While a single detection reagent may be utilized in the present packaging, it is contemplated that a plurality of detection reagents compositions are utilized to maximize capabilities for detecting more than one explosive chemical. The plurality of detection reagents may be disposed directly or indirectly on any support structure. For example, the detection reagents may be disposed directly on the substrate 100 or indirectly on the substrate by being disposed on a liner 300 that is attached to the substrate or on a geometric shaped platform disposed on said support structure. A suggested tolerance for each of the plurality of detection reagent in relation to each other and to the desired collection wipe is +0.03 inches. Should the detection reagents be disposed on a platform, the composition and characteristics of the platform may be the same as described for the collection platform 220.

The detection reagents may be permanently affixed to the packaging support structure either through the use of adhesives, silicones, or any equivalent method that would affix the detection reagents in a way so that its surface is sufficiently exposed so that it may be diluted when it comes in contact to the sample located on the collection pad surface 230. Any method that is chosen to affix the reagents must not negatively affect, degrade, or harm the performance of the detection or colorimetric response. When assembled with the packaging, the detection reagents must be in a sealed environment to prevent oxidation of the reagents once inside the package. The prevention of oxidation can occur by any means (including removable covers) that does not degrade, negatively affect, or harm the reagents, colorimetric detection, and humans that will come in contact with the product.

The examples provided herein utilizes a circle for the shape of the reagent composition, however, any shape, size, pattern, and configuration for the detection reagent can be used so long as those physical parameters permit contact with the sample collection pad surface 230.

The detection reagents contemplated for use with the explosive detection packaging may be in solid or liquid form. If the detection reagent is in a liquid form, i.e. neat or dissolved or dispersed in a solvent, it is contemplated that the liquid detection reagent is pre-saturated or pre-soaked onto an asborbant material. The liquid detection reagent may be individually packaged to avoid contamination until it is ready to be contacted with the collected sample. At that time, any barrier material covering the liquid detection reagent may be removed and the detection reagent contacted with the sample collection pad surface. The absorbant material may use the same type of material and platform (if needed) as described above for the collection assembly. The pre-soaked solution of the detection reagent may also contain preservatives and freezing point suppression additives. These optional additives should have similar characteristics as described for solvents, i.e. safe for human and inert to the chemical detection reaction.

The dimensions of an embodiment for the explosive detection packaging may be 7.5 inches long, 2.25 inches wide, and 0.35 inches in height with a tolerance of ±0.0625 inches. The overall size and tolerances of the package may be reduced or increased depending on the intended use of the product. The dimensions and configuration of the explosive detection kit described herein enables the kit to be small enough to store in pockets or cases and yet provides the capabilities to detect multiple explosives.

The location of the collection assembly, detection reagents, and covers may vary. Any location may be utilized on the packaging for each of the components, however, the respective components should be arranged on the flexible package in such a manner that when the package is folded over, the detection reagents (either in solid or liquid pre-soaked on absorbant material) contacts a corresponding sample collection pad and do not cross-contaminate other samples or reagents. Any contemplated configuration of the detection reagents and collection assembly should allow for separate compartments and sealed off areas segregating the reagents and collection assembly to avoid contamination from storage or actual use. This ensures that the packaging and chemistry can effectively detect multiple types of explosives with one sample. The explosive detection kit can be used for bulk or trace explosive samples and can identify multiple types of explosive materials from one sample at the same time.

Explosive Detection Reagents

The packaging disclosed herein allows for a plurality of detection reagent compositions to be assembled within a single packaging. The present invention contemplates reagent compositions that may be useful for detecting one or more of the following components found in explosives including: inorganic nitrates (including the alkali and alkaline earth metal salts, ammonium salts and urea salts); chlorates; perchlorates; hydrogen peroxide and organic peroxides (particularly triacetone peroxide, hexamethylene triperoxide diamine, and methyl ethyl ketone peroxide); urea; nitrate esters including: nitroglycerin, nitrocellulose, erythritol tetranitrate, pentaerythritol trinitrate, pentaerythritol tetranitrate, nitrated starch, nitrated cane sugar, ethylene glycol dinitrate, diethylene glycol dinitrate, triethylene glycol dinitrate, propylene glycol dinitrate, trimethylolethane trinitrate, trimethylolmethane trinitrate, and butanetriol trinitrate; nitramines including: cylcotrimethylenetrinitramine, cyclotetramethylenetetranitramine and 2,4,6,8,10,12-hexanitrohexaazaisowurtzitane; nitroaromatics including: mono, di, and trinitrophenol, mono, di, and trinitroresorcinol (and salts thereof), mono, di, and trinitrotoluene/benzene, and trinitrophenylmethylnitramine; and nitroparaffins including nitromethane, tetranitromethane, and hexanitroethane.

Examples of detection reagents compositions that may be useful for the explosive detection kits are described as follows:

Reagent Composition for Chlorate and Hydrogen Peroxide Detection

A novel composition of ruthenium and ethylenediaminetetraacetate (EDTA) complex (Ru-EDTA), binuclear aromatic hydroxyl (BAH), and an optional ancillary salt in solid form for detecting and differentiating explosive residues containing chlorates and hydrogen peroxide is described herein. Such composition not only differentiates between chlorates and hydrogen peroxide but also exhibit improved color strength and response time which is ideal for detecting explosive residues.

Ru-EDTA complexes alone including its pendadentate ligand complex (RuHEDTA) and tetradentate ligand complex (Ru-H2EDTA) exhibit the same colorimetric response in the presence of chlorates or hydrogen peroxide oxidizers, independent of concentration or physical state. The results in FIGS. 20-25 illustrates that use of Ru-EDTA complexes alone and independent of concentration, and in either solution or solid form provides minimal color differences over time and the color differentiation between chlorates and hydrogen peroxide are nearly indistinguishable. Color response was measured with a spectrodensitometer (model 528 from X-Rite, Grand Rapids, Mich.) to obtain the numerical values for cyan (c), magenta (m), and yellow (y) components.

Figure 20:
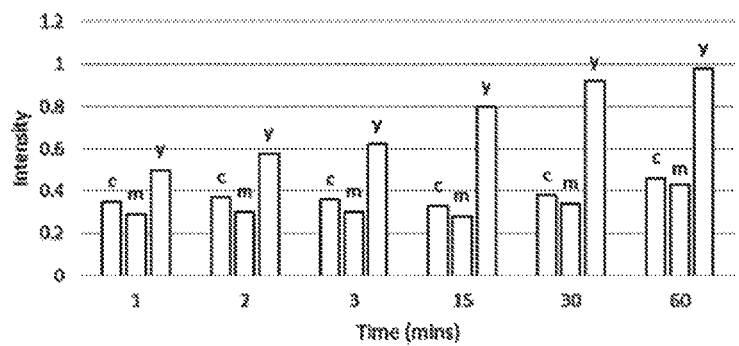
FIG. 20 is a chart for oxidation of dilute RuH2EDTA with a) potassium chlorate and b) hydrogen peroxide.
Figure 20:
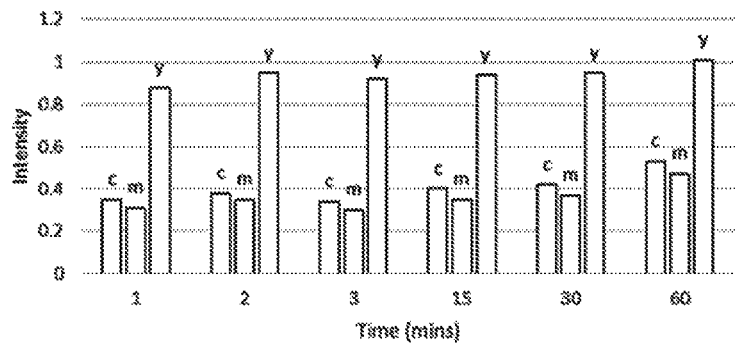
Figure 21:
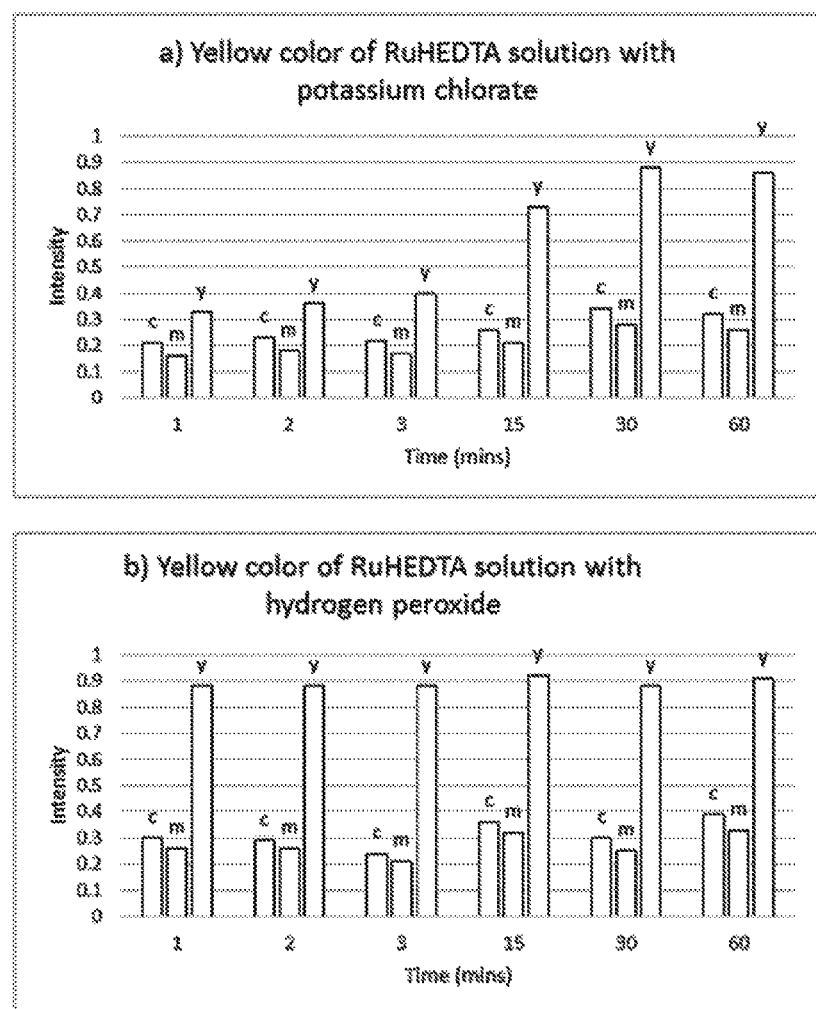
FIG. 21 is a chart for oxidation of dilute RuHEDTA with a) potassium chlorate and b) hydrogen peroxide.

The results in FIGS. 20 and 21 were generated by preparing Ru-EDTA as follows: liquid solutions of RuH2EDTA and RuHEDTA were prepared by dissolving 2 mg of each complex in 10 mL of a solution of 0.2 M sodium acetate-acetic acid buffer that contained 14% by weight of dimethyl formamide (DMF). To each solution was added oxidant in excess of the required amount for the reaction to be complete. In the case of potassium chlorate this was set to about 50% molar excess and over 400% molar excess of hydrogen peroxide was used (these values were based on equal mass quantities of explosives). The excess of oxidant was used to ensure full color development.

Figure 22:
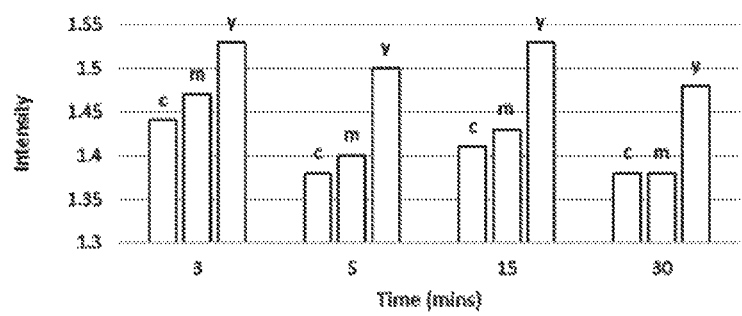
FIG. 22 is a chart for oxidation of concentrated RuH2EDTA with a) potassium chlorate and b) hydrogen peroxide.
Figure 22:
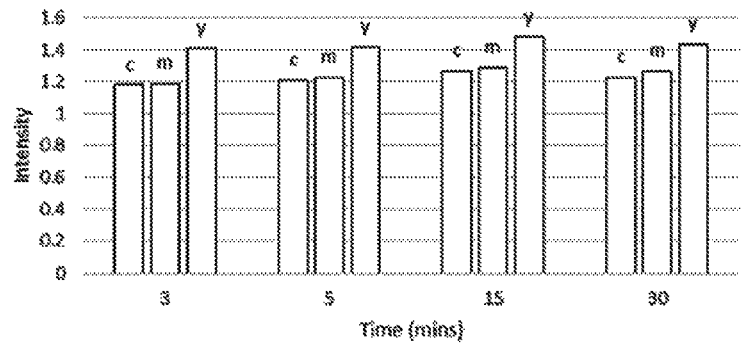
Figure 23:
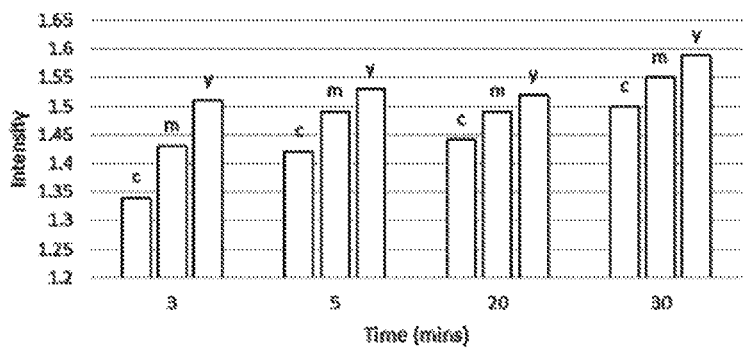
FIG. 23 is a chart for oxidation of concentrated RuHEDTA with a) potassium chlorate and b) hydrogen peroxide.
Figure 23:
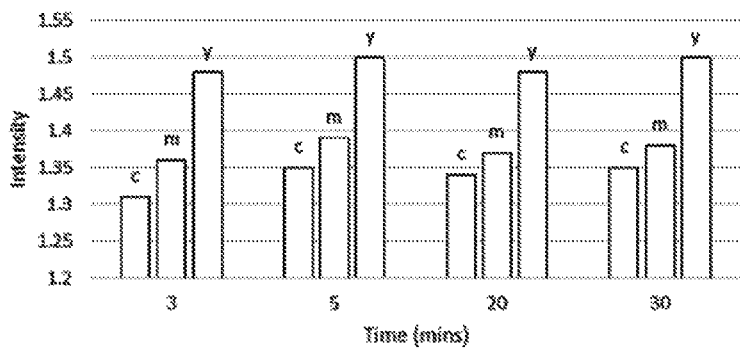

Increasing the concentration of Ru-EDTA in solution also did not exhibit color differentiation. FIGS. 22 and 23 illustrates that increasing the concentration of the Ru-EDTA complexes exhibited a characteristic green color but not color differentiation was observed. In this set of experiments the ratio of oxidant to ruthenium remained the same as in the dilute experiments.

Figure 24:
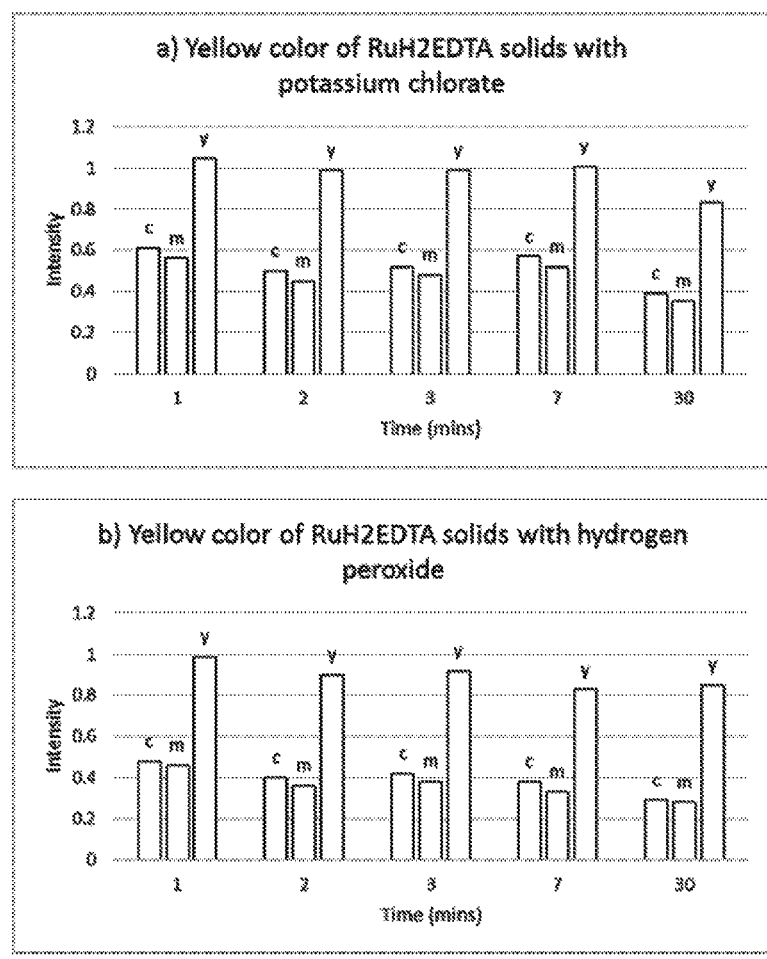
FIG. 24 is a chart for oxidation of RuH2EDTA solids with a) potassium chlorate and b) hydrogen peroxide.
Figure 25:
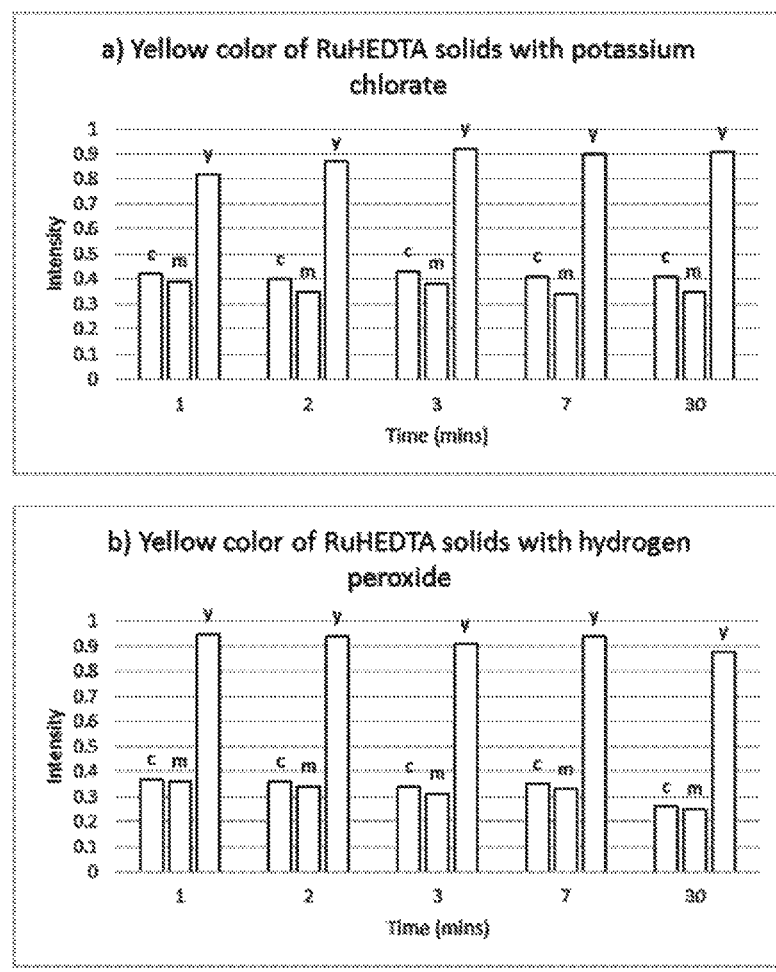
FIG. 25 is a chart for oxidation of RuHEDTA solids with a) potassium chlorate and b) hydrogen peroxide.

Increasing the concentration of Ru-EDTA in a solid state also did not exhibit color differentiation. FIGS. 24 and 25 illustrates that neither Ru-EDTA complex provides ideal color differentiation upon oxidation. Although the color development is good, the color differentiation is inconclusive.

Figure 26:
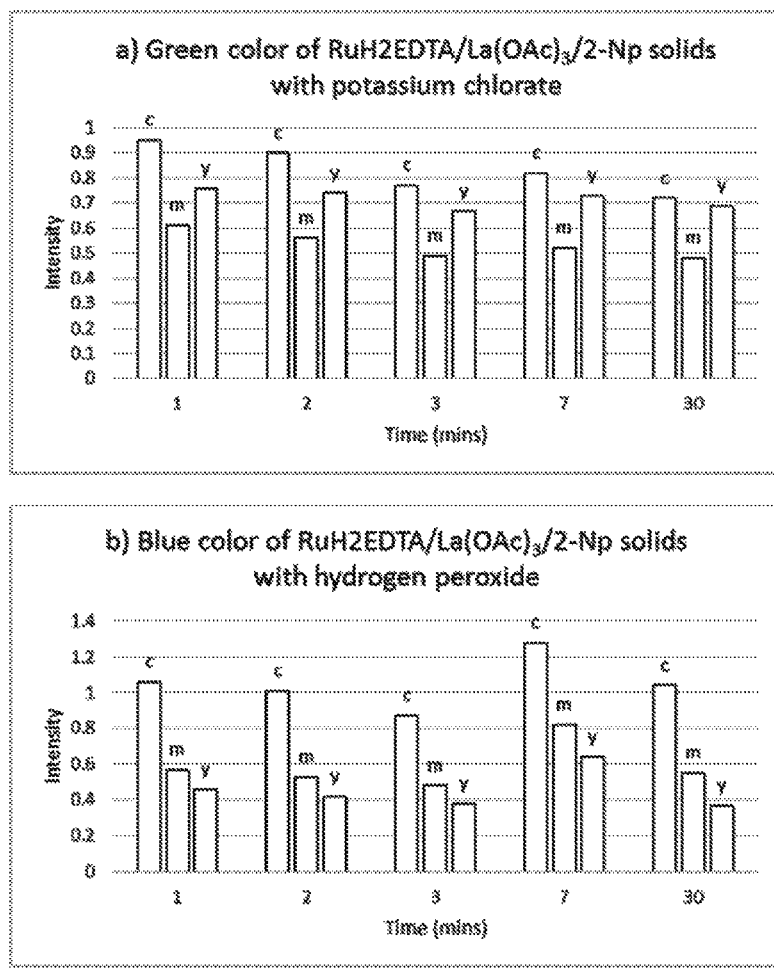
FIG. 26 is a chart for oxidation of RuH2EDTA/La(OAc)$_3$/2-Np solids with a) potassium chlorate and b) hydrogen peroxide.
Figure 27:
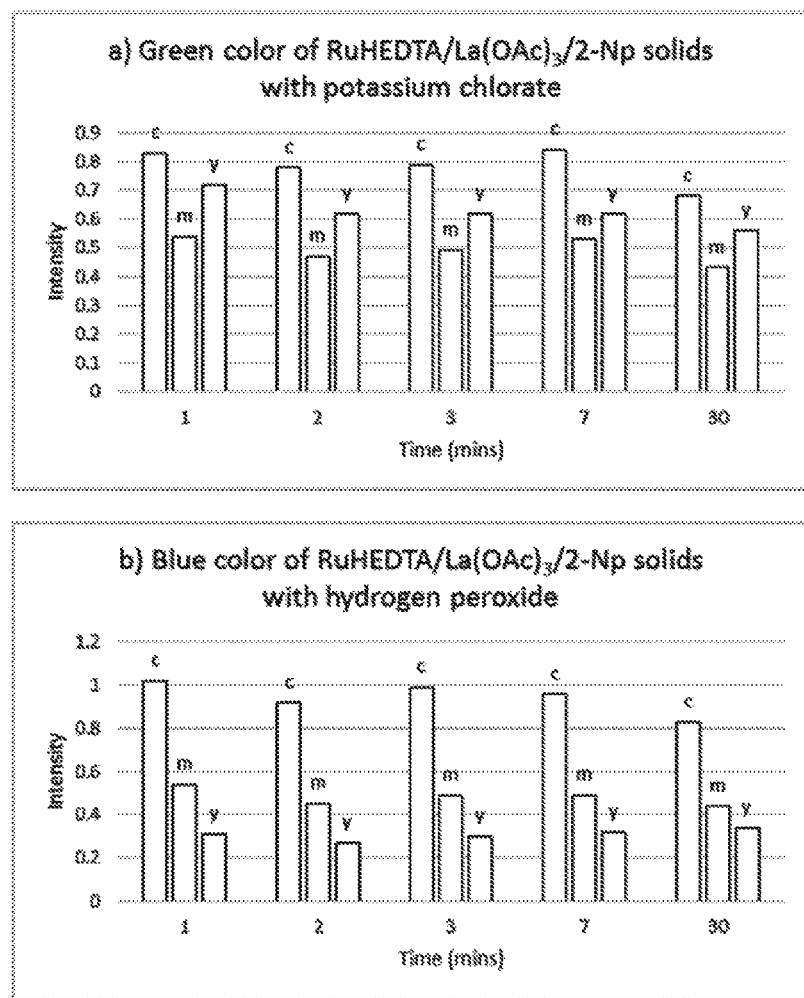
FIG. 27 is a chart for oxidation of RuHEDTA/La(OAc)$_3$/2-Np solids with a) potassium chlorate and b) hydrogen peroxide.

In contrast, the novel compositions disclosed herein comprising Ru-EDTA, lanthanum acetate and 2-naphthol indicate exceptional color differentiation and development within 1 minute. In one embodiment, the novel composition in solid form, comprising 2.5 parts Ru-EDTA, 37.4 parts lanthanum acetate and 12 parts 2-naphthol were prepared by grinding the components and mixing them together. The solid composition was tested against potassium chlorate and hydrogen peroxide. Results from the experiments are reported in FIGS. 26 and 27.

Figure 28:
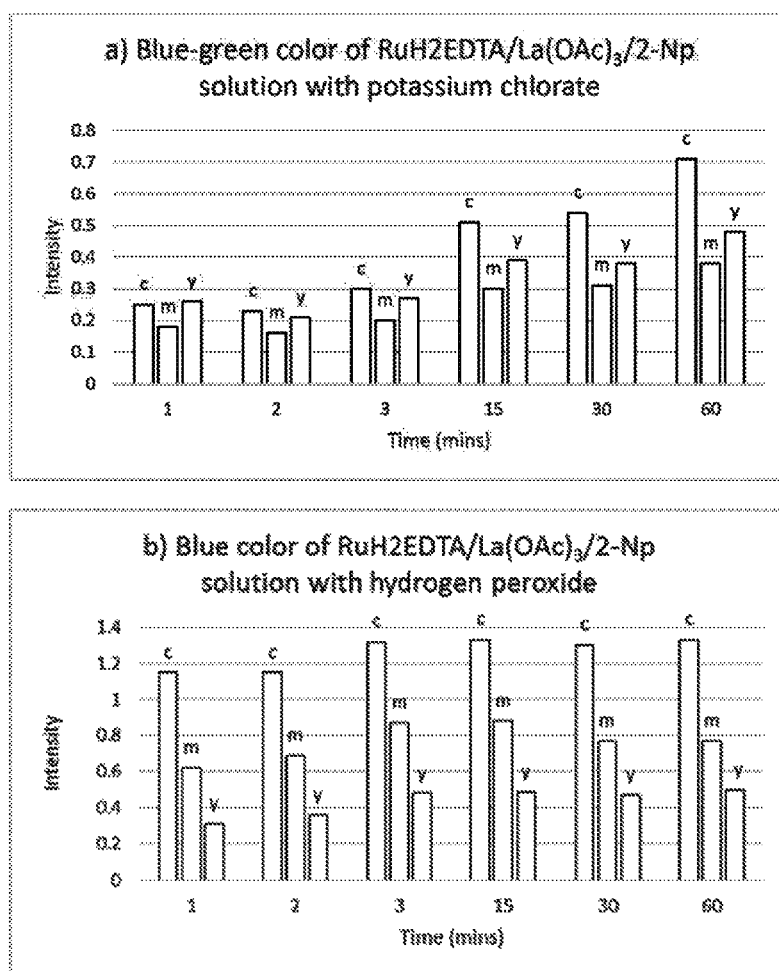
FIG. 28 is a chart for oxidation of dilute RuH2EDTA/La(OAc)$_3$/2-Np solutions with a) potassium chlorate and b) hydrogen peroxide.
Figure 29:
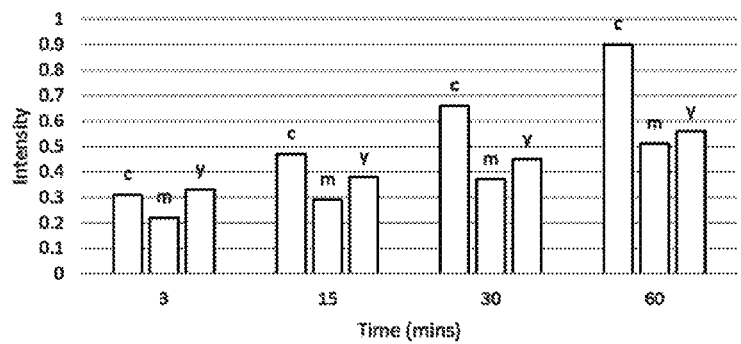
FIG. 29 is a chart for oxidation of dilute RuHEDTA/La(OAc)$_3$/2-Np solutions with a) potassium chlorate and b) hydrogen peroxide.
Figure 29:
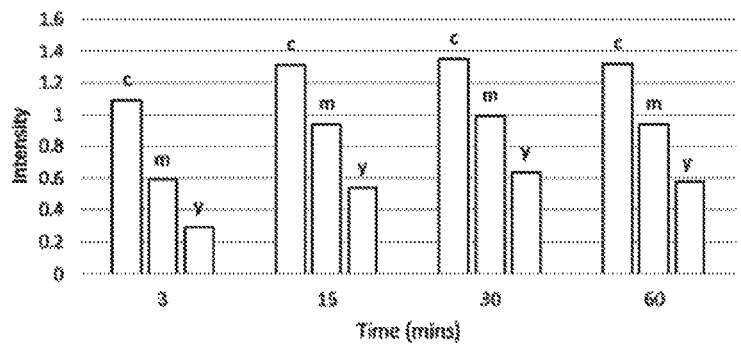
Figure 30:
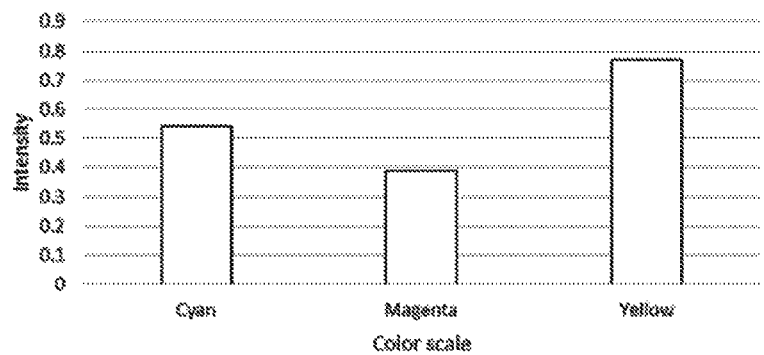
FIG. 30 is a chart for oxidation of dilute RuH2EDTA/La(OAc)$_3$/2-Np solutions with a) potassium chlorate and b) hydrogen peroxide overnight.
Figure 30:
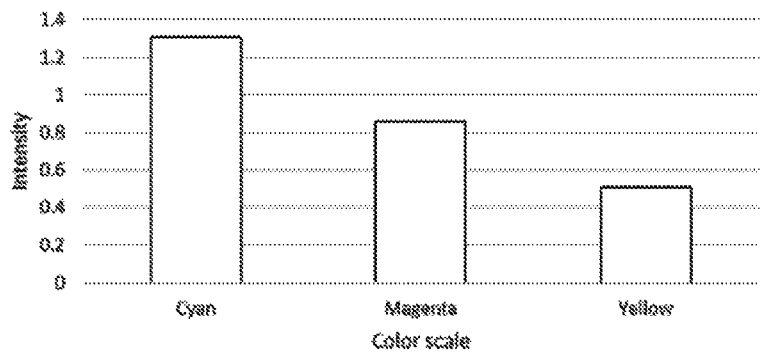

Liquid solutions of the novel composition were also evaluated for explosive detection. FIGS. 28 and 29 shows the oxidation of dilute solutions of the novel formulation but color differentiation was considerably more difficult to ascertain within a reasonable time frame. Color development was an intense blue with hydrogen peroxide but the pale blue response of chlorate is difficult to qualify as either "green" or "blue." Color differentiation is finally achieved with the RuH2EDTA, lanthanum acetate, and 2-naphthol overnight (FIG. 30), but not so with RuHEDTA, lanthanum acetate, and 2-naphthol which turned brown and slightly turbid with the chlorate sample overnight.

The Ru-EDTA complexes described herein can be prepared in either its diprotonated (RuH2EDTA) or monoprotonated (RuHEDTA) form in accordance with the process described below.

Preparation of potassium dichloro(ethylenediaminetetraacetato) ruthenate (111) hydrate (KRuCl2[H2EDTA]) abbreviated as Ru[H2EDTA] was as follows: 775 mg (3.7 mmol) of ruthenium (III) chloride was added to a round bottomed flask equipped with a magnetic bar containing 60 mL conc. HCl under an argon blanket and mixed at room temperature. The flask was equipped with a condenser and the mixture was heated to reflux for two hours. The reflux was interrupted and 280 mg (3.7 mmol) of potassium chloride and 2 g (10 mmol) of mercury were added to the flask. Reflux was continued under vigorous mixing for two additional hours. The heating was stopped and the flask submerged in an ice bath. The contents of the flask were filtered to remove solids and the filtrate was charged to a simple distillation apparatus equipped with heating mantle. The contents were distilled down to a black tar of near dryness.

The contents of the flask were cooled to room temperature under argon and to this was added 40 mL of deionized water followed by 1.4 g (3.7 mmol) of disodium ethylenediaminetetraacetate with stirring. The resulting dark green mixture was heated to reflux for 15 minutes then cooled to room temperature overnight under argon. The following day 25 mL of 1 mM $HClO_4$ was added to the flask and the contents heated to reflux with stirring for 30 minutes followed by simple distillation with a heating mantle to afford orange solids of near dryness. The contents of the flask were cooled under argon to room temperature and filtered and washed with deionized water followed by methanol and diethyl ether to obtain 1.24 g of yellow solid (75% yield). Alkaline titrimetric analysis was consistent with the literature which describes equivalence points for the deprotonation of two uncoordinated carboxylic acid groups and one water ligand.

Preparation of potassium chloro(ethylenediaminetetraacetato) ruthenate (III) hydrate (KRuCl[HEDTA]) abbreviated as Ru[HEDTA] was prepared as follows: 775 mg (3.7 mmol) of ruthenium (III) chloride was added to a round bottomed flask equipped with a magnetic bar containing 60 mL conc. HCl under an argon blanket and mixed at room temperature. The flask was equipped with a condenser and the mixture was heated to reflux for two hours. The reflux was interrupted and 280 mg (3.7 mmol) of potassium chloride and 2 g (10 mmol) of mercury were added to the flask. Reflux was continued under vigorous mixing for two additional hours. The heating was stopped and the flask submerged in ice bath. The contents of the flask were filtered to remove solids and the filtrate was charged to a simple distillation apparatus equipped with heating mantle. The contents were distilled down to a black tar of near dryness. The contents of the flask were cooled to room temperature under argon and 40 mL of deionized water followed by 1.4 g (3.7 mmol) of disodium ethylenediaminetetraacetate were added to the flask with stirring followed by simple distillation to remove 25 mL of distillate. This produced an aqueous suspension of solids that were filtered and washed with deionized water to obtain 840 mg of brown solid (44% yield). Alkaline titrimetric analysis was consistent with the literature which describes equivalence points for deprotonation of one uncoordinated carboxylic acid group and one water ligand.

Preferred BAH compounds include 2-naphthol, 3-hydroxy-2-naphthoic acid, 6-hydroxy-2-naphthalenesulfonic acid, and 4-hydroxy-1-naphthalenesulfonic acid and their derivatives. More preferred BAH compounds are 2-naphthol and 1- and 2-naphthol derivatives. Some BAH compounds such as those which contain amino groups may be unsuitable for colorimetric detection. For instance, 3-amino-2-naphthol interfered with the color change due to the formation of a purplish gray color when mixed with Ru-EDTA and partially dissolved. Mononuclear aromatic hydroxy compounds such as phenol and phenol derivatives were also evaluated but did not improve the color response. For example, phenol and 4-ethyl resorcinol when combined with the initially yellow Ru-EDTA complexes produced brown colors in the presence of chlorate which were challenging to detect. Other compounds such as 2,6-dichlorophenol when combined with Ru-EDTA did not change color in the presence of chlorate.

Preferred lanthanum salts contemplated for the present invention include lanthanum acetate, lanthanum phosphate, lanthanum chloride, gadolinium acetate and ytterbium acetate and more preferably lanthanum acetate, lanthanum phosphate, and lanthanum chloride.

Figure 1:
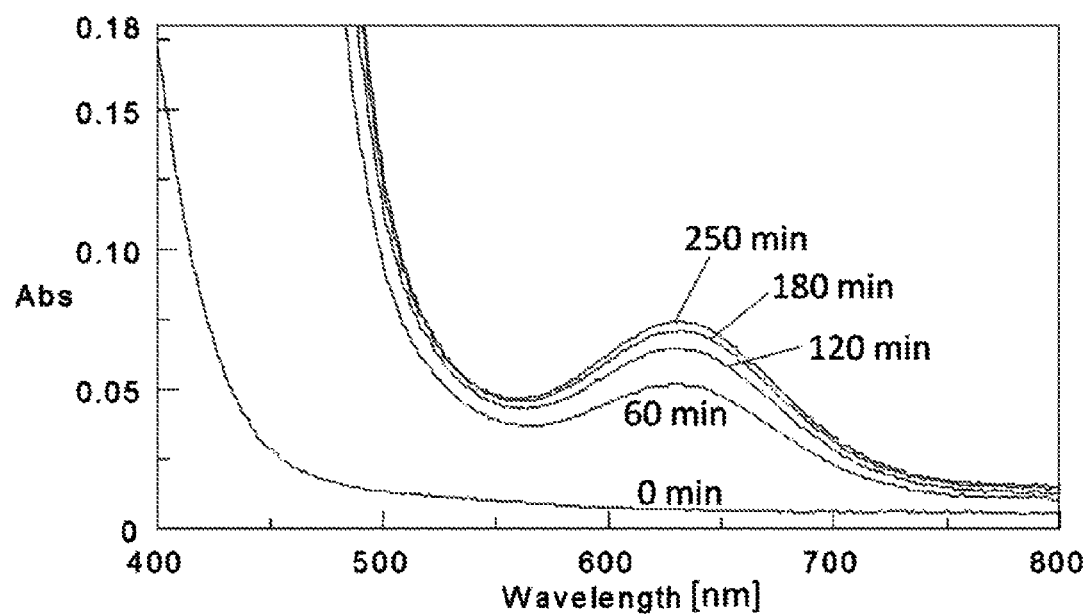
FIG. 1 is a graph illustrating the effect of Ru-EDTA alone on its oxidation of chlorate at time 0.
Figure 2:
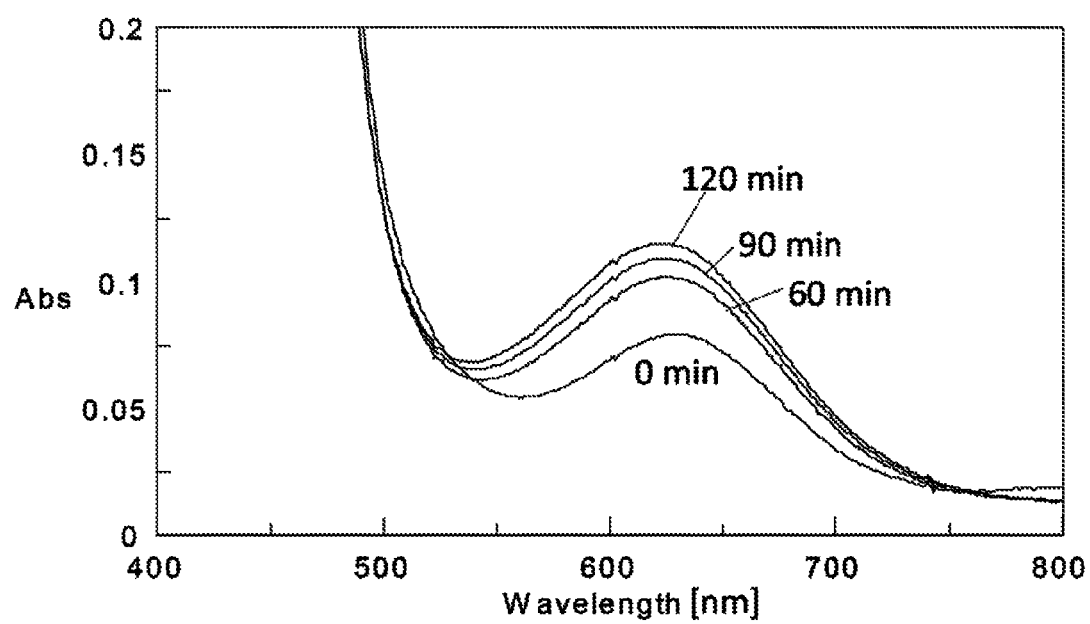
FIG. 2 is a graph illustrating the effect of Ru-EDTA on its oxidation of chlorate when 2-naphthol was added at time 250 min.

FIGS. 1 and 2 illustrates the effect of Ru-EDTA on its oxidation of chlorate when 2-naphthol Was added. In FIG. 1, a sample containing 3 mL of a 0.56 mM aqueous solution of Ru-EDTA (1.68×10-3 mmol) was prepared in 0.2 M sodium acetate-acetic acid buffer (pH 4.7) with 14% by weight DMF and mixed with a 30% molar excess of potassium chlorate (1.8×10-4 mmol) at time zero observed over time using UV/Visible spectroscopy, model V-660 spectrophotomer from Jasco, Inc., Easton, Md. Ru-EDTA oxidation by chlorate to form a mixed valence ruthenium oxide dimer was observed with an increase of absorbance at 630 nm wavelength. After the mixed valence ruthenium oxide dimer was fully formed, a solution of 34 µL of 50 mM 2-naphthol (1.68×10-3 mmol) prepared in DMF was added and monitored over time to show a further increase in the absorbance peak at 630 nm. This indicates a reaction between 2-naphthol and the mixed valence ruthenium oxide dimer as shown in FIG. 2. In a similarly performed experiment HPLC analysis verified the decrease of 2-naphthol in the presence of ruthenium oxide dimer.

Experiments

In one embodiment, a white non-reacting laboratory wipe such as a folded Kimwipe (Kimberly-Clark, Dallas Tex.) moistened with water to collect the suspected area that contains either chlorate or hydrogen peroxide residue is used. After the explosive is collected the Kimwipe is placed into an aluminum dish containing between 1 and 2 mg of accurately weighed solids composition of a mixture of Ru-EDTA/BAH/lanthanum salt. The Kimwipe with collected explosive is lightly rubbed into the solids composition mixture for several seconds in a rotating fashion to allow for the intimate contact of explosive with the composition to occur. The Kimwipe is then set aside for visual observation. Within seconds a dramatic color change to green or blue begins to develop in the presence of explosive and within one minute the color development strengthens to clearly indicate the presence of potassium chlorate or hydrogen peroxide, respectively.

A most preferred explosive detection composition contains 5% Ru-EDTA, 72% lanthanum acetate, and 23% 2-naphthol by weight. A slight but acceptable decrease in color strength is seen when the Ru-EDTA is reduced in a composition that contained 1.2% Ru-EDTA, 74.8% lanthanum acetate, and 24% 2-naphthol by weight. An increase of Ru-EDTA over 5% is also acceptable.

The limit of detection (LOD) of either potassium chlorate or hydrogen peroxide with the most preferred formula is suitable down to 10 µg for detection within one minute. Even better LOD is possible when the response time is extended beyond one minute. Bulk detection of either potassium chlorate or hydrogen peroxide with the composition disclosed here is practically instantaneous.

Due to the subjective nature of color formation (hue and strength) a spectrodensitometer (model 528 from X-Rite, Grand Rapids, Mich.) was employed for evaluation although it is understood that the average color sensitive person would capably discern color formation without the need for instrumentation. The spectrodensitometer was calibrated against a white standard and displays numerically the color wheel according to visual intensity and individual cyan, magenta, and yellow components. Tables 1 and 2 list the results of detection for potassium chlorate and hydrogen peroxide placed on aluminum foil and subsequently wiped with a laboratory wipe such as a folded Kimwipe moistened with water. It is clearly evident from the tables that color detection was superior when a mixture of Ru-EDTA/BAH/La salt/was used. The combination of Ru-EDTA with BAH was critical in all cases for a color change to occur and the addition of lanthanum salt was necessary for color development in the case of chlorate detection but not required for hydrogen peroxide, although in all experiments the lanthanum salt intensified the color strength. Not shown in the tables is the fact that in the absence of Ru-EDTA no color change occurs with any combination of BAH and/or lanthanum salt with chlorates or hydrogen peroxide.

Table 1.

Spectrodensitometer values for the detection of 60 µg of potassium chlorate on laboratory wipe with 1-2 mg of formulation at room temperature (average of at least three readings). Formulation is proportional to 2.5 parts Ru-EDTA, 37.4 parts La salt, and 12 parts BAH by weight.

| Item | Formulation* | Visual Intensity | Cyan | Magenta | Yellow | Color at 1 minute |
|---|---|---|---|---|---|---|
| 1 | Ru[HEDTA] | 0.39 | 0.36 | 0.43 | 0.85 | yellow |
| 2 | Ru[HEDTA]/La(OAc)$_3$ | 0.35 | 0.36 | 0.36 | 0.52 | yellow |
| 3 | RutHEDTA]2-Np | 0.34 | 0.37 | 0.32 | 0.57 | yellow |
| 4 | Ru[HEDTA]/La(OAc)$_3$/2-Np | 0.64 | 0.73 | 0.56 | 0.83 | green |
| 5 | Ru[H2EDTA] | 0.33 | 0.30 | 0.39 | 0.82 | yellow |

-continued

| Item | Formulation* | Visual Intensity | Cyan | Magenta | Yellow | Color at 1 minute |
|---|---|---|---|---|---|---|
| 6 | Ru[H2EDTA]/La(OAc)₃ | 0.33 | 0.36 | 0.34 | 0.96 | yellow |
| 7 | Ru[H22EDTA]/2-Np | 0.14 | 0.13 | 0.14 | 0.35 | yellow |
| 8 | Ru[H2EDTAna(OAc)₃/2-Np | 0.54 | 0.64 | 0.46 | 0.66 | green |
| 9 | Ru[HEDTA]/La(OAc)₃/4-HNSA | 0.67 | 0.78 | 0.57 | 0.84 | green |
| 10 | Ru[HEDTA]/La(OAc)₃/6-HNSA | 0.93 | 1.10 | 0.79 | 0.82 | blue shade green |
| 11 | Ru[H2EDTA]/La(OAc)₃/3-HNA | 0.57 | 0.68 | 0.47 | 0.65 | green |
| 12 | Ru[H2EDTA]/La(OAc)₃/4-HNSA | 0.57 | 0.65 | 0.48 | 0.74 | green |
| 13 | Ru[H2EDTA]/La(OAc)₃/6-HNSA | 0.83 | 0.99 | 0.69 | 0.72 | green |

*La(OAc)₃: lanthanum acetate, 2-Np: 2-naphthol, 3-HNA: 3-hydroxy-2-naphthoic acid, 4-HNSA: 4-hydroxy-1-naphthalenesulfonic acid, 6-HNSA: 6-hydroxy-2-naphthalenesulfonic acid Table 2.

Spectrodensitometer values for the detection of 60 μg of hydrogen peroxide on laboratory wipe with 1-2 mg of formulation at room temperature (average of at least three readings). Formulation is proportional to 2.5 parts Ru-EDTA, 37.4 parts La salt, and 12 parts BAH by weight.

| Item | Formulation* | Visual Intensity | Cyan | Magenta | Yellow | Color at 1 minute |
|---|---|---|---|---|---|---|
| 1 | Ru[HEDTA] | 0.48 | 0.45 | 0.54 | 1.01 | yellow |
| 2 | Ru[HEDTA]/La(OAc)₃ | 0.44 | 0.47 | 0.45 | 1.08 | yellow |
| 3 | Ru[HEDTA]/2-Np | 0.74 | 0.84 | 0.64 | 0.79 | blue |
| 4 | Ru[HEDTA]/La(OAc)₃/2-Np | 0.98 | 1.18 | 0.81 | 0.61 | blue |
| 5 | Ru[H2EDTA] | 0.32 | 0.29 | 0.36 | 0.78 | yellow |
| 6 | Ru[H2EDTA]/La(OAc)₃ | 0.38 | 0.39 | 0.39 | 0.96 | yellow |
| 7 | Ru[H2EDTA]/2-Np | 0.75 | 0.83 | 0.67 | 0.85 | blue |
| 8 | Ru[H2EDTA]/La(OAc)₃/2-Np | 0.97 | 1.11 | 0.85 | 0.79 | blue |

*La(OAc)₃: lanthanum acetate, 2-Np: 2-naphthol

Reagent Composition for Ammonia and Urea Detection

Compositions for detecting of ammonium ion and urea commonly found in homemade explosives are also contemplated. Disclosed herein is a two step process for detecting ammonium and urea using a first detection reagent composition comprising sodium phenoxide and a second detection reagent composition comprising sodium dichloroisocyanurate (SDCC), sodium carbonate, and sodium nitroprusside Detection of the ammonium ion and urea uses the indophenol reaction, a fast colorimetric reaction that involves a sequence of steps to produce a unique colored complex with either ammonium or urea. The components of the reaction employs an oxidizing agent and a phenolic compound which react under basic conditions with ammonium or urea to form compounds known as indophenols. The resulting ammonium ion produces a blue colored complex and the urea complex appears initially as a yellow color but changes to green over time.

Examples of oxidizing agents contemplated include sodium hypochlorite, calcium hypochlorite or sodium dichloroisocyanurate (SDCC). Examples of phenolic compounds include phenol, 2,6-dichlorophenol, thymol or salicylic acid.

It has been determined that the reactivity of the indophenol reaction is greatly enhanced with an iron catalyst, to permit the color response to occur at room temperature on a time scale suitable for explosives detection. Examples of iron catalyst suitable for the present detection reagents include sodium nitroprusside and potassium hexacyanoferrate.

The indophenol reaction mechanism is illustrated by the following reaction process for ammonium detection.

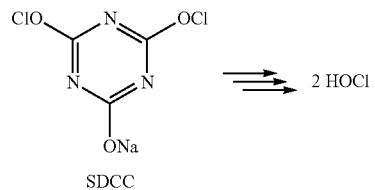

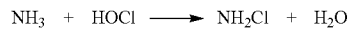

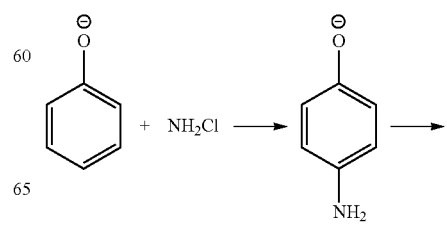

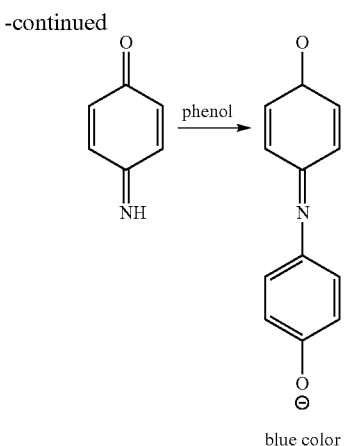

blue color

The indophenol reaction mechanism is illustrated by the following reaction process for urea detection.

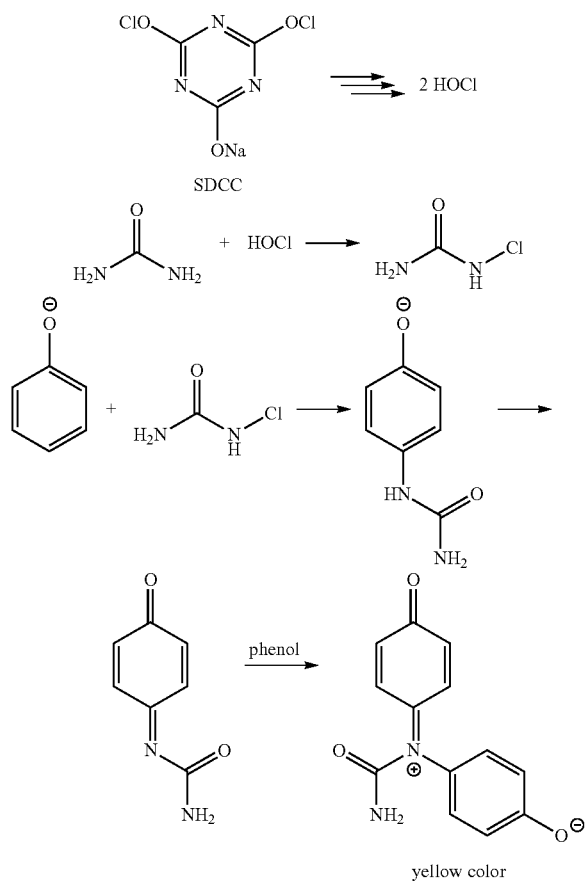

yellow color

The composition for detecting ammonium and urea comprises sodium dichloroisocyanurate (SDCC), sodium carbonate, sodium nitroprusside and sodium phenoxide. In contrast to prior known compositions using wet solution analysis for detecting ammonium and urea in explosives, the present composition uses solid detection reagents in a sequential fashion resulting in positive detection in less than one minute. The sodium phenoxide reagent is isolated from the mixture of SDCC/sodium carbonate/sodium nitroprusside until the detection procedure is initiated; otherwise, discoloration due to reactive incompatibilities may occur. This can be accomplished by separately positioning the SDCC/sodium carbonate/sodium nitroprusside detection reagent composition at a separate location from the sodium phenoxide reagent composition on the packaging structure.

The method for detecting ammonium ion and urea comprises intimately contacting a solid detection reagent composition containing sodium phenoxide with the collection pad surface 230 containing solvent and urea or ammonia substrate explosive residue. To ensure intimate contact, it is preferred that the solid reagent sodium phenoxide is pressed against the collection pad surface 230 firmly for a few seconds. Thereafter, a second solid detection reagent composition comprising SDCC, sodium carbonate and sodium nitroprusside is contacted with the previously contacted collection pad surface containing sodium phenoxide, solvent and explosive residue. The composition comprising SDCC, sodium carbonate and sodium nitroprusside reagents may be pressed against the collection pad surface firmly for a few seconds to ensure sufficient contact for the chemical reaction to occur indicated by a change in color observed on the collection pad surface. The sequence of contacting the reaction with the collection pad surface may be reversed such that the composition comprising SDCC, sodium carbonate and sodium nitroprusside is placed in contact with the collection pad surface first followed by the sodium phenoxide detection reagent composition.

Figure 18:
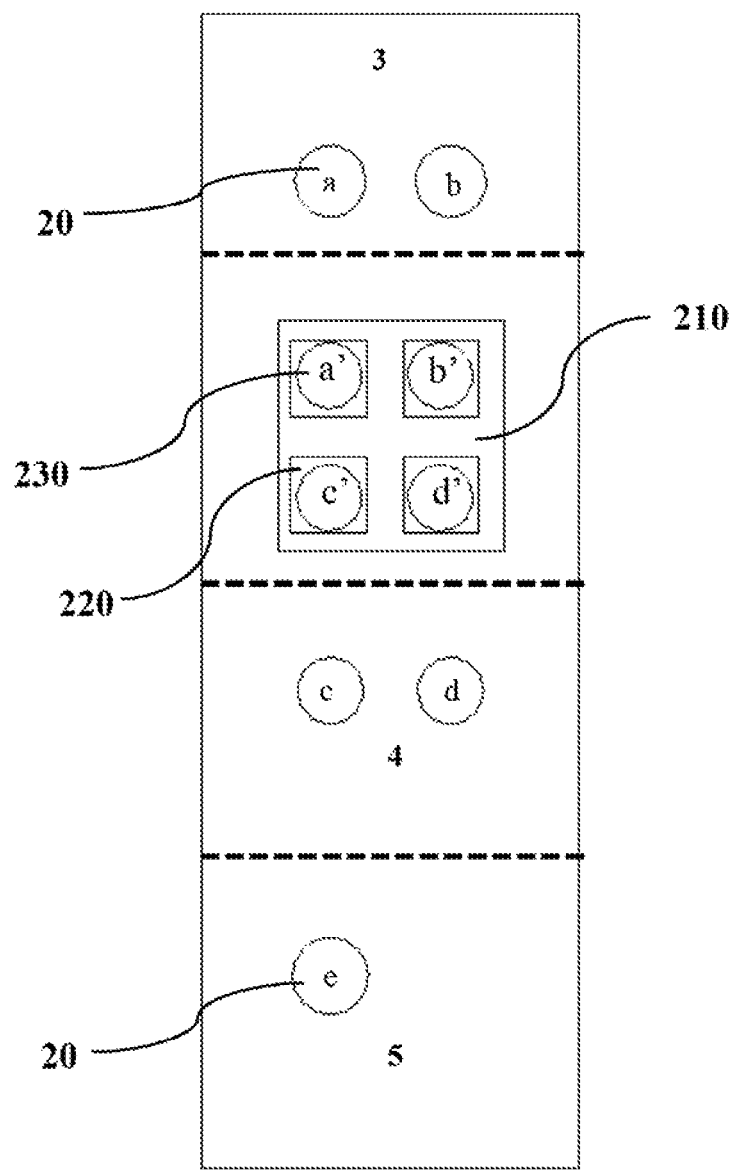
FIG. 18 is a perspective view of an explosive detection kit of the first embodiment with the covers removed indicating the sequence for contacting the detection reagent with the corresponding collection pad surface.

FIG. 18 illustrates placement of the immediately described solid reagent compositions and the methods for using the reagent composition for detecting ammonia and urea. Referring to FIG. 18, a first reagent detection composition c is placed in intimate contact with collection pad surface c' saturated with a solvent such as water. Thereafter, a second detection reagent e is placed in intimate contact with the same collection pad surface c' to complete the chemical reaction. A reference standard 500 is provided as an example wherein an observed color response is compared against the reference standard 500. The presence of yellow to green color on the collection pad indicates the presence of urea in the explosive residue and an observed color response appearing as blue may indicate the presence of ammonium ion in an ammonia containing explosive.

Table 3 illustrates a preferred composition for the urea and ammonia detection reagent. The preferred composition is formulated for detecting 15 micrograms of ammonium and urea at one minute. The formulation is adjusted to a fixed value of 100 parts of SDCC. The total quantity of sodium phenoxide is equal to the total quantity of combined SDCC/sodium nitroprusside/sodium carbonate (1-2 mg of combined total). In other words there is no more than 2 mg of total solids in which case 1 mg is sodium phenoxide and 1 mg is SDCC/sodium nitroprusside/sodium carbonate.

TABLE 3

| Ingredients | Range | Comments |
| --- | --- | --- |
| SDCC | 100 (fixed) | Oxidizer necessary for reaction to occur. |
| Sodium nitroprusside | 1.5-10 | Catalyst. Below 1.5 no color detection. Above 10 no improvement seen. |
| Sodium carbonate | 100-300 | Base. Outside of range no improvement seen. Formulations without sodium carbonate show longer color response time. |

TABLE 3-continued

| Ingredients | Range | Comments |
|---|---|---|
| Sodium phenoxide | Amount fixed to equal the combined parts of SDCC/sodium nitroprusside/sodium carbonate | Substrate necessary for color change. Actual quantity not critical for color response. |

Reagent Composition for Nitrate Detection

A composition containing a mixture of either tartaric or citric acid, sulfanilamide, N-(1-Naphthyl)ethylenediamine dihydrochloride, and zinc powder is described herein for detecting nitrates present in military and homemade explosives. Nitrates contemplated for detection by the composition disclosed herein include ammonium nitrate, urea nitrate, potassium nitrate, and calcium ammonium nitrate.

The chemistry of detection is based on a reaction known as the Griess reaction, which involves the formation of a highly colored azo compound from a bimolecular reaction. The Griess reaction is a fast colorimetric reaction which begins with the reaction of a nitrite molecule to initiate a diazonium salt with an aromatic amine which subsequently combines with a second aromatic compound to form a colored azo compound. The addition of zinc in the reaction acts as a catalyst to allow for the facile reduction of nitrate into nitrite. The Griess reaction has many variations which includes different aromatic compounds and choice of catalysts. The overall Griess chemical reaction scheme is commonly depicted as follows:

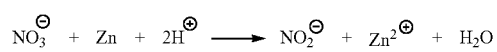

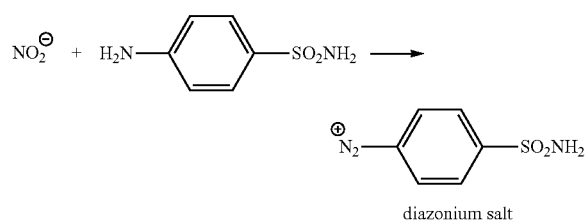

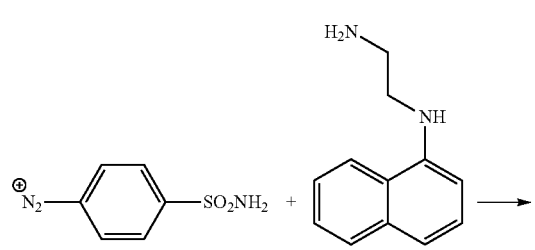

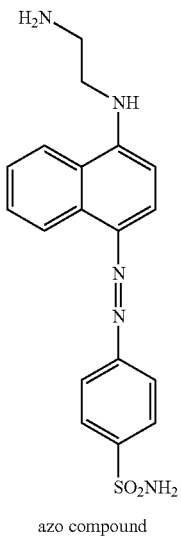

azo compound

The utility of the Griess reaction is widespread and includes analyses of nitrates in environmental, food, industrial and physiological systems. Commercial kits are common and available to allow for the rapid detection of nitrates. For example, soil, water, and food analysis may be performed with a NECi Lab Nitrate Test kit from The Nitrate Elimination Company, Inc. of Lake Linden, Mich. which uses an enzymatic reduction of nitrate to nitrite to initiate the Griess reaction. Another example is a physiological test kit for the estimation of nitric oxide (which forms nitrite in situ) for biological systems from Molecular Probes of Eugene, Oreg. This kit contains a different aromatic compound without the need of a catalyst, but nonetheless, still relies on the Griess reaction for its detection.

Explosives detection has also benefited from the commercialization of the Griess reaction. Pocket ETK™ from Lindon Defense of East Providence, R.I. uses the Griess reaction to detect inorganic nitrates disclosed in U.S. Pat. No. 5,296,380. In addition, Plexus Scientific Corporation of Alexandria, Va. offers two products for nitrate detection: Expray and Drop-Ex which uses either an aerosol or liquid form, respectively.

The drawback for these commercial explosives detection products for detecting inorganic nitrates uses wet chemical analysis requiring reagents to be dispensed and mixed in a sequential fashion for the chemical reaction to occur.

The detection reagent composition as disclosed herein does not require wet analysis but instead uses solid reagents affixed to the disclosed package system. The reagent composition for detecting inorganic nitrates comprises intimate ground mixture of either tartaric or citric acid, sulfanilamide, N-(1-Naphthyl)ethylenediamine dihydrochloride, and zinc powder.

The process for detection requires collection of the inorganic nitrate sample onto a water moistened laboratory wipe followed by contact of the wipe with the nitrate detection composition comprising: either tartaric or citric acid, sulfanilamide, N-(1-Naphthyl)ethylenediamine dihydrochloride, and zinc powder and held for a count of three seconds. The wipe is then removed and observed for a color response within one minute. The presence of nitrate produces a pink color.

An equal amount of sulfanilamide and N-(1-Naphthyl) ethylenediamine dihydrochloride is required for the reaction to proceed to completion. The quantity of tartaric or citric acid must be in a sufficient amount to create an acidic environment to allow the reaction to proceed to completion (refer to Griess chemical reaction scheme above). An excess of acid is also preferred to ensure that any possible basic "contaminants" that may be present with the nitrate are neutralized so as not to interfere with the reaction. The amount of zinc catalyst is suggested below. A preferred formulation for the nitrate detection composition for detecting 10 micrograms of ammonium nitrate at one minute is set forth below in Table 4.

TABLE 4

Preferred reagent composition for the explosives detection of 10 micrograms of ammonium nitrate with 1-2 mg of finely ground mixture.

| Ingredients | Amount | Comments |
| --- | --- | --- |
| Tartaric or citric acid | Two moles | Excess ensures acidic environment necessary for the reaction. |
| Sulfanilamide | One mole | Fixed amount based on stoichiometry |
| N-(1-Naphthyl)ethylenediamine dihydrochloride | One mole | Fixed amount based on stoichiometry |
| Zinc powder | 1.7 to 4.5 moles | (Catalyst) Slight decrease in color response seen at 1.7 moles. Quantity of zinc above 4.5 moles darkens background color excessively. |

Methods for Explosives Detection

Detection for explosive residue is performed by the following steps: (1) exposing collection pad 230; (2) contacting the suspected explosive residue with the collection pad 230; (3) exposing the detection reagent 20; (4) contacting the detection reagent 20 with the collection pad 230 containing the sample; (5) and observing the color change for comparison against a reference standard 500 to determine the presence and type of explosive. The process of step (4) may be repeated with more than one detection reagent 20 and a corresponding collection pad.

FIGS. 17-20 illustrates an example for using the explosive detection kit disclosed herein.

Figure 17:
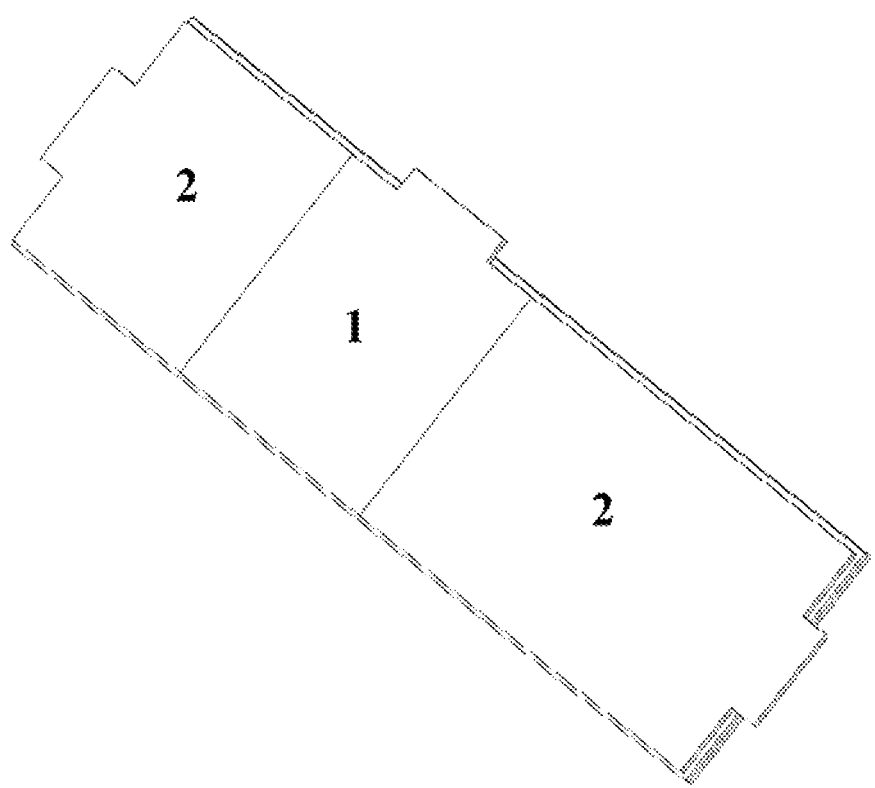
FIG. 17 is a perspective view of a fully assembled explosive detection kit of the first embodiment, indicating the sequence for removal of the protective covers.

Step (1) exposing the collection pad surface. In FIG. 17, the cover 420 protecting the collection assembly is first removed exposing the collection assembly 200.

Step (2) contacting the suspected explosive material with the wet collection pad surface. In FIG. 18, the exposed collection pad surface 230 is placed in contact with the suspected explosive material by any means to facilitate collection of the suspected explosive residue on the collection pad. This can be accomplished by wiping, rubbing, or swabbing etc.

Step (3) removing the covers 410 and 430. The protective covers 410 and 430 over the detection reagents are removed to exposed the plurality of detection reagents 20. The sequence of cover removal is illustrated by the numbers indicated in FIG. 17.

Step (4) contacting the detection reagent 20 with the collected sample on the collection pad surface 230. The detection reagents affixed to the packaging element (in FIG. 18, the detection reagent compositions are affixed to the liner) are folded over so that the detection reagents are in intimate contact with the collection pad surface containing suspected explosive residue. Contact of the detection reagents with the collection pad surface may be repeated for different reagents depending on the type of explosive indicated for detection. For example, FIG. 18 illustrates the sequential steps for contacting a plurality of detection reagents with the collection pad surface. A plurality of detection reagents 20 (a, b, c, and d) are affixed on the liner of the package, lateral to the collection pad 230. Detection reagent a and detection reagent b is folded over and place in contact with the corresponding collection pad surface a' and b'. The detection reagent composition may be pressed firmly against the collection pad surface for a few seconds to ensure intimate contact of the detection reagent, solvent and explosive residue sample. Additional steps of contacting the detection reagent with the collection pad surface may be repeated depending on the type of explosives to be detected. For example in FIG. 18, detection reagent c and detection reagent d may be folded over and place in contact with its corresponding collection pad surface c' and d'. Additional detection reagents may be contacted with the same collection pad surface for multiple chemical reactions as described for detecting ammonium ion and urea for example.

Figure 19:
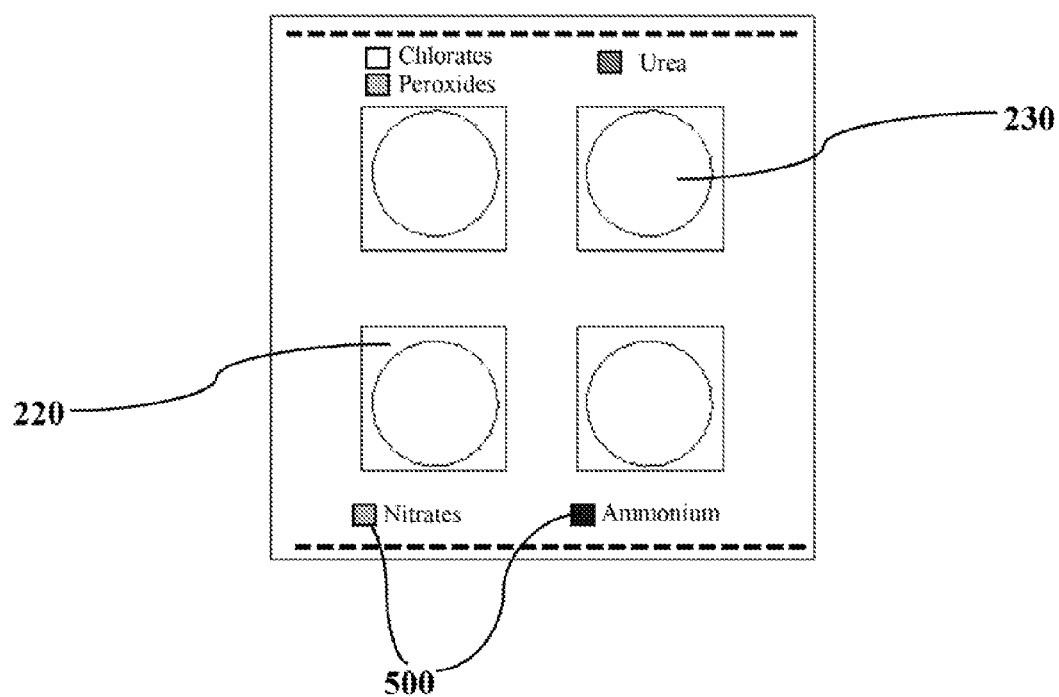
FIG. 19 is a top view of the reference explosive material of the first embodiment color coded to the type of explosive material.

Step (5) detecting a color change for presence of explosive. In less than 1 minute after contacting the detection reagent, solvent and explosive residue, a colorimetric response may be indicated by a change in color on the collection pad surface if an explosive material is present. The color change is compared agains a reference standard 500 that is included with the explosive detection kit to identify the specific types of explosive material. The reference standard 500 may be printed on the explosive package itself as illustrated in FIG. 19 or elsewhere on the packaging that does not interfere with the chemical reaction between the collected explosive residue and the detection reagent composition.

Although the present invention has been explained in relation to its preferred embodiments, it is to be understood that many other possible modifications and variations can be made without departing from the scope and spirit of the invention as hereinafter claimed.

What is claimed is:

1. An explosive detecting reagent composition comprising, rutheniumethylenediaminetetraacetate (Ru-EDTA) complex, and a binuclear aromatic hydroxyl (BAH) compound wherein said BAH compound is absent amino groups, and wherein said explosive detecting reagent composition is a solid.

2. The composition of claim 1, wherein the BAH compound is selected from the group consisting of 2-naphthol, 3-hydroxy-2-naphthoic acid, 6-hydroxy-2-naphthalenesulfonic acid, and 4-hydroxy-1-naphthalenesulfonic acid.

3. The composition of claim 1, wherein the Ru-EDTA complex is monoprotonated or diprotonated.

4. The composition of claim 1, further comprising an ancillary salt.

5. The composition of claim 1, wherein the ancillary salt is a lanthanide salt.

6. The composition of claim 1, wherein the Ru-EDTA complex is greater than 1%.

7. The composition of claim 1, wherein the Ru-EDTA complex is about 1% to about 5%.

8. The composition of claim 1 wherein the Ru-EDTA is about 1-5% by weight, the lanthanum acetate is about 72% by weight, and 2-naphthol is about 23% by weight.

9. An explosive detecting reagent composition comprising Rutheniumethylenediaminetetraacetate (Ru-EDTA) complex, 2-naphthol, and lanthanum acetate and wherein said explosive detecting composition is a solid.

10. An explosive detection kit comprising:
   A flexible packaging and a reagent detection composition comprising rutheniumethylenediaminetetraacetate (Ru-EDTA) complex, and a binuclear aromatic hydroxyl (BAH) compound wherein said BAH compound is absent amino groups, wherein the reagent detection composition is disposed on the flexible packaging.

11. The flexible packaging of claim 10, comprising a substrate, collection pad and cover.

12. A method for detecting explosives comprising the sequential steps of:
   contacting a surface containing suspected explosive residue with collection material wherein the suspected explosive residue adheres to the collection material;
   contacting the composition of claim 1 to the collection material comprising the suspected explosive residue; and
   comparing a color change of said suspected explosive residue to a reference standard.

13. The method of claim 12, wherein the explosive residue comprises a chlorate or hydrogen peroxide compound.

14. The method of claim 12, wherein the collection material comprises a liquid solvent.

15. The method of claim 12, wherein the color change is green or blue color.

* * * * *